US009657064B2

(12) United States Patent
Derouazi et al.

(10) Patent No.: US 9,657,064 B2
(45) Date of Patent: May 23, 2017

(54) CELL PENETRATING PEPTIDES

(71) Applicants: UNIVERSITE DE GENEVE, Geneva (CH); Les Hopitaux Universitaires De Geneve, Geneva (CH)

(72) Inventors: Madiha Derouazi, Grand-Saconnex (CH); Paul Walker, Viry (FR); Pierre-Yves Dietrich, St Julien en Genevois (FR)

(73) Assignees: LES HOPITAUX UNIVERSITAIRES DE GENEVE, Geneva (CH); UNIVERSITE DE GENEVE, Geneva (CH)

( * ) Notice: Subject to any disclaimer, the term of this patent is extended or adjusted under 35 U.S.C. 154(b) by 0 days.

(21) Appl. No.: 14/427,459

(22) PCT Filed: Sep. 12, 2013

(86) PCT No.: PCT/IB2013/058497
§ 371 (c)(1),
(2) Date: Mar. 11, 2015

(87) PCT Pub. No.: WO2014/041505
PCT Pub. Date: Mar. 20, 2014

(65) Prior Publication Data
US 2015/0239938 A1 Aug. 27, 2015

Related U.S. Application Data

(60) Provisional application No. 61/700,432, filed on Sep. 13, 2012.

(30) Foreign Application Priority Data

Sep. 13, 2012 (EP) .................................. 12184311

(51) Int. Cl.
| A61K 47/48 | (2006.01) |
| C07K 7/08 | (2006.01) |
| C07K 14/05 | (2006.01) |
| C07K 19/00 | (2006.01) |
| C07K 14/005 | (2006.01) |
| C07K 14/77 | (2006.01) |
| A61K 38/16 | (2006.01) |
| A61K 39/00 | (2006.01) |

(52) U.S. Cl.
CPC ...... *C07K 14/005* (2013.01); *A61K 47/48246* (2013.01); *C07K 7/08* (2013.01); *C07K 14/05* (2013.01); *C07K 14/77* (2013.01); *A61K 38/162* (2013.01); *A61K 39/00* (2013.01); *C07K 2319/10* (2013.01); *C12N 2710/16222* (2013.01); *C12N 2740/16122* (2013.01); *C12N 2760/18522* (2013.01)

(58) Field of Classification Search
CPC ...... A61K 38/03; A61K 38/10; A61K 38/162; A61K 39/245; A61K 47/48246; A61K 47/4833; C07K 4/02; C07K 7/08; C07K 14/05; C07K 2319/10; C12N 2710/16222
See application file for complete search history.

(56) References Cited

U.S. PATENT DOCUMENTS

| 6,093,794 A * | 7/2000 | Barney ................ C07K 5/0806 424/186.1 |
| 6,337,180 B1 | 1/2002 | Drouet et al. |
| 2008/0044407 A1 | 2/2008 | Strome et al. |
| 2009/0047307 A1* | 2/2009 | Harrop .................. A61K 31/00 424/232.1 |
| 2012/0052080 A1 | 3/2012 | Okada |
| 2012/0214744 A1 | 8/2012 | Bourdoulous et al. |
| 2012/0231030 A1 | 9/2012 | Derouazi et al. |
| 2013/0116201 A1 | 5/2013 | Lenormand et al. |

FOREIGN PATENT DOCUMENTS

| WO | WO-99/59615 A1 | 11/1999 |
| WO | WO-01/51673 A2 | 7/2001 |
| WO | WO-2011/036211 A1 | 3/2011 |
| WO | WO-2011/101332 A1 | 8/2011 |
| WO | WO-2011/135222 A2 | 11/2011 |

OTHER PUBLICATIONS

Wang et al. A Redox-Sensitive Cysteine in Zta Is Required for Epstein-Barr Virus Lytic Cycle DNA Replication. Journal of Virology. Nov. 2005, vol. 79, No. 21, pp. 13298-13309.*
Antón, L., et al. (1997), "MHC Class I-Associated Peptides Produced from Endogenous Gene Products with Vastly Different Efficiencies", *The Journal of Immunology*, 158: 2535-2542.
Brooks, N. et al. (2010), "Cell-penetrating peptides: Applicantion in vaccine delivery", *Biochimica et Biophysica Acta*, 1805: 25-34.
Derouazi, M., et al. (2010), "Towards an Efficient DC Vaccine by Antigenic Protein Loading Using a Novel Protein Transduction Domain", *Poster at 11th International Symposium on Dendritic Cells in Fundamental and Clinical Immunology—DC 2010*, Palazzo dei Congressi, Lungano—Sep. 26 to Sep. 30, 2010.
Durántez, M., et al. (2008), "Induction of Multiepitopic and Long-Lasting Immune Responses Against Tumour Antigens by Immunization with Peptides, DNA and Recombinant Adenoviruses Expressing Minigenes", *Scandinavian Journal of Immunology*, 69: 80-89.
Ishioka G., et al. (1999), "Utilization of MHC Class I Transgenic Mice for Development of Minigene DNA Vaccines Encoding Multiple HLA-Restricted CTL Epitopes", *The Journal of Immunology*, 162: 3915-3925.
Mateo, L., et al. (1999), "An HLA-A2 Polyepitope Vaccine for Melanoma Immunotherapy", *The Journal of Immunology*, 163: 4058-4063.

(Continued)

*Primary Examiner* — Jeffrey E Russel
(74) *Attorney, Agent, or Firm* — Harness, Dickey and Pierce, P.L.C.

(57) ABSTRACT

The present invention relates to a short cell penetrating peptide derived from the Epstein-Barr virus basic leucine zipper transcriptional activator (ZEBRA), optionally linked to a cargo molecule. It also relates to a complex comprising the cell penetrating peptide and a cargo molecule, as well as cells loaded with the complex and the use thereof in therapy and diagnosis.

21 Claims, 3 Drawing Sheets

(56) References Cited

OTHER PUBLICATIONS

McPherson, S., et al. (2003), Resting CD8 T cells recognize β-galactosidase expressed in the immune-privileged retina and mediate autoimmune disease when activated, *Immunology*, 110: 386-396.

NCBI Reference YP01673.1—BZLF1 [Human herpesvirus 4]—Protein—www.ncbi.nlm.nih.gov/protein/YP_401673—3 pages (download Feb. 6, 2014).

Rosenzweig, M., et al. (2001), "Induction of cytotoxic T lymphocyte and antibody responses to enhanced green fluorescent protein following transplantation of transduced CD 34+ hematopoietic cells", *Blood*, 97(7): 1951-1959.

Rothe, R., et al. (2008), "Expression and Purification of ZEBRA Fusion Proteins and Applications for the Delivery of Macromolecules into Mammalian Cells", *Current Protocols in Protein Science*, Supplemental 54(18): 11.1-11.29.

Rothe, R., et al. (2010), "Characterization of the Cell-penetrating Properties of the Epstein-Barr Virus ZEBRA trans-Activator", *The Journal of Biological Chemisry*, 285(26): 20224-20233.

Rothe, R., et al. (2010), "PhD Thesis—Caracterisation de la propriété de la Protéine ZEBRA du virus Epstein-Barr á pénétrer dans les cellules", *Universite De Grenoble*, 156 pages.

Scardino, A., et al. (2007), "A Polyepitope DNA Vaccine Targeted to Her-2/ErbB-2 Elicits a Broad Range of Human and Murine CTL Effectors to Protect against Tumor Challenge", *Cancer Research*, 67(14): 7028-7036.

Stubbs, A., et al. (2001), "Whole recombinant yeast vaccine activates dendritic cells and elicits protective cell-mediated immunity", *Nature Medicine*, 7(5): 625-629.

Thomson, S., et al. (1995), "Minimal epitopes expressed in a recombinant polyepitope protein are processed and presented to CD8+ cytotoxic T cells: Implications for vaccine design", *Proc. Natl. Acad. Sci. USA.*, 92: 5845-5849.

Thomson, S., et al. (1996), "Recombinant Polyepitope Vaccines for the Delivery of Multiple CD8 Cytotoxic T Cell Epitopes", *The Journal of Immunology*, 157: 822-826.

Tine, J., et al. (2005), "Enhanced multiepitope-based vaccines elicit CD8+ cytotoxic T cells against both immunodominant and cryptic epitopes", *Vaccine*, 23: 1085-1091.

Tünnemann, G., et al. (2006), "Cargo-dependent mode of uptake and bioavailability of TAT-containing proteins and peptides in living cells", *The FASEB Journal*, 20: 1775-1784.

van Montfoort, N., et al. (2009), "Antigen storage compartments in mature dendritic cells facilitate prolonged cytotoxic T lymphocyte cross-priming capacity", *PNAS*, 106(16): 6730-6735.

Waeckerle-Men, Y., et al. (2005), "Dendritic cell-based multi-epitope immunotherapy of hormone-refractory prostate carcinoma", *Cancer Immunol Immunother*, 55: 1524-1533.

International Search Report and Written Opinion dated Jan. 8, 2014 issued in PCT Patent Application No. PCT/IB2013/058497.

\* cited by examiner

E     F

CPP1+ova    CPP2+ova

CELL PENETRATING PEPTIDES

PRIORITY STATEMENT

This application is a national stage application under 35 U.S.C. §371 of PCT International Application No. PCT/IB2013/058497, which has an international filing date of 12 Sep. 2013 and claims priority under 35 U.S.C. §119 to European Patent Application No. 12184311.4 filed 13 Sep. 2012 and the benefit of U.S. Provisional Patent Application No. 61/700,432 filed 13 Sep. 2012. The contents of each application recited above are incorporated herein by reference in their entirety

FIELD OF THE INVENTION

The present invention relates to new cell penetrating peptides as cellular delivery agents for biological and medical applications.

BACKGROUND OF THE INVENTION

The plasma membrane of eukaryotic cells is a tightly controlled barrier protecting the cell from unregulated influx of bioactive molecules. For small-molecule and protein or other macromolecule-based drugs that are not endogenous to the cell, traversing the plasma membrane can involve either using a natural transport system or achieving direct diffusion through the lipid bilayer. However, in many cases, both modes of entry are inefficient for exogenous molecules.

In the past decade, cell penetrating peptides (CPPs) have emerged as promising vectors to deliver different therapeutic agents, including proteins, to their targets. CPPs are peptide sequences facilitating efficient protein translocation across biological membranes, independently of transporters or specific receptors. CPPs also offer the advantage of cost-efficient production. Since the discovery 20 years ago of the membrane translocating property of human immunodeficiency virus transactivating regulatory protein (HIV TAT), several CPPs have been identified including penetratin (Antennapedia homeodomain), VP22 (Herpes simplex virus) and the synthetic polyarginine (polyR). Different cargoes have been linked to CPPs with the perspective of novel vaccine design.

Recently, the Epstein-Barr virus basic leucine zipper transcriptional activator ZEBRA was shown to cross the outer membrane of live cells and to accumulate in the nucleus of lymphocytes. More particularly, it has been demonstrated that the minimal region of ZEBRA, which is necessary for the cell-penetrating ability of the Epstein-Barr virus ZEBRA trans-activator, spans from residue 170 to residue 220 of ZEBRA and that both the DNA binding domain and the dimerization domain contained in that region are necessary for the cell-penetrating properties (Rothe et al. 2010, *J. Biological Chemistry* 285(26): 20224-20232).

Many CPPs have drawbacks when their use as vehicles for delivery of cargo molecules into the cell is considered. For instance, they can cause severe side-effects in the cell such as cytoplasmic leakage due to membrane disruption or interference with the normal functioning of membrane proteins, or can cause cellular toxic effects and/or immunogenic effects. Also, some CPPs may be rapidly degraded in the cytoplasm or remain entrapped in endosomes to be degraded in lysosomes. Moreover, some CPPs are unable to release the cargo molecule, or do not have a broad spectrum for addressing or releasing the cargo molecule.

Therefore, there is still a need for an improved vehicle able to deliver a wide variety of cargo molecules into a cell, which exhibits a high efficiency of uptake of the cargo molecule as well as low toxicity. In the context of vaccines, it would also be advantageous if the delivery vehicle was not restricted to only one pathway for internalization of the cargo molecule and could be delivered to both the cytosol and endosomes for antigen presentation. The present invention solves this problem by providing CPPs which allow efficient delivery and presentation of, for instance, antigenic determinants at the cell surface of antigen presenting cells. The CPPs of the invention, thus, are useful as vehicles for delivery of a variety of cargo molecules such as polypeptides and proteins, polysaccharides, lipids, or combinations thereof, as well as nucleic acids, small molecule drugs, and imaging agents.

SUMMARY OF THE INVENTION

A first aspect of the invention provides a cell penetrating peptide characterized in that:
  a) the length of the amino acid sequence of said peptide is comprised between 15 and 30 amino acids in total; and
  b) said peptide has an amino acid sequence comprising a fragment of the region extending from residue 170 to residue 220 of ZEBRA, wherein, optionally, 1, 2, 3, 4, or 5 amino acids have been substituted, deleted and/or added without aborting said peptide's cell penetrating ability;
  or a variant of said peptide comprising an amino acid sequence having at least one conservatively substituted amino acid compared to said peptide's amino acid sequence.

A second aspect of the invention relates to a complex comprising said cell penetrating peptide and a cargo molecule.

A third aspect of the invention concerns polynucleotides encoding said cell penetrating peptide or said complex, as well as vectors containing such polynucleotides.

A fourth aspect of the invention resides in host cells expressing a cell penetrating peptide or a complex as defined above, as well as methods of producing such cells.

A fifth aspect of the invention relates to cells loaded with the complex as defined above.

A sixth aspect of the invention concerns compositions comprising: (i) a cell penetrating peptide of the invention, (ii) a complex of the invention, (iii) a nucleic acid of the invention, (iv) a vector of the invention, (v) a host cell of the invention, or (vi) cells loaded with a complex according to the invention.

A seventh aspect of the invention concerns the compositions mentioned above for use as medicaments or for use as imaging or diagnostic compositions.

An eighth aspect of the invention is a kit-of-parts comprising at least one of:
  (a) a cell penetrating peptide according to the invention;
  (b) a complex according to the invention;
  (c) a nucleic acid according to the invention;
  (d) a vector according to the invention;
  (e) a host cell according to the invention;
  (f) a cell loaded with a complex according to the invention.

A ninth aspect of the invention provides a method for delivering a cargo molecule into a cell in vitro, comprising the step of placing said cell into contact with a cell penetrating peptide according to the invention and said cargo molecule.

Other features and advantages of the invention will be apparent from the following detailed description.

DETAILED DESCRIPTION OF THE INVENTION

Figure 1:
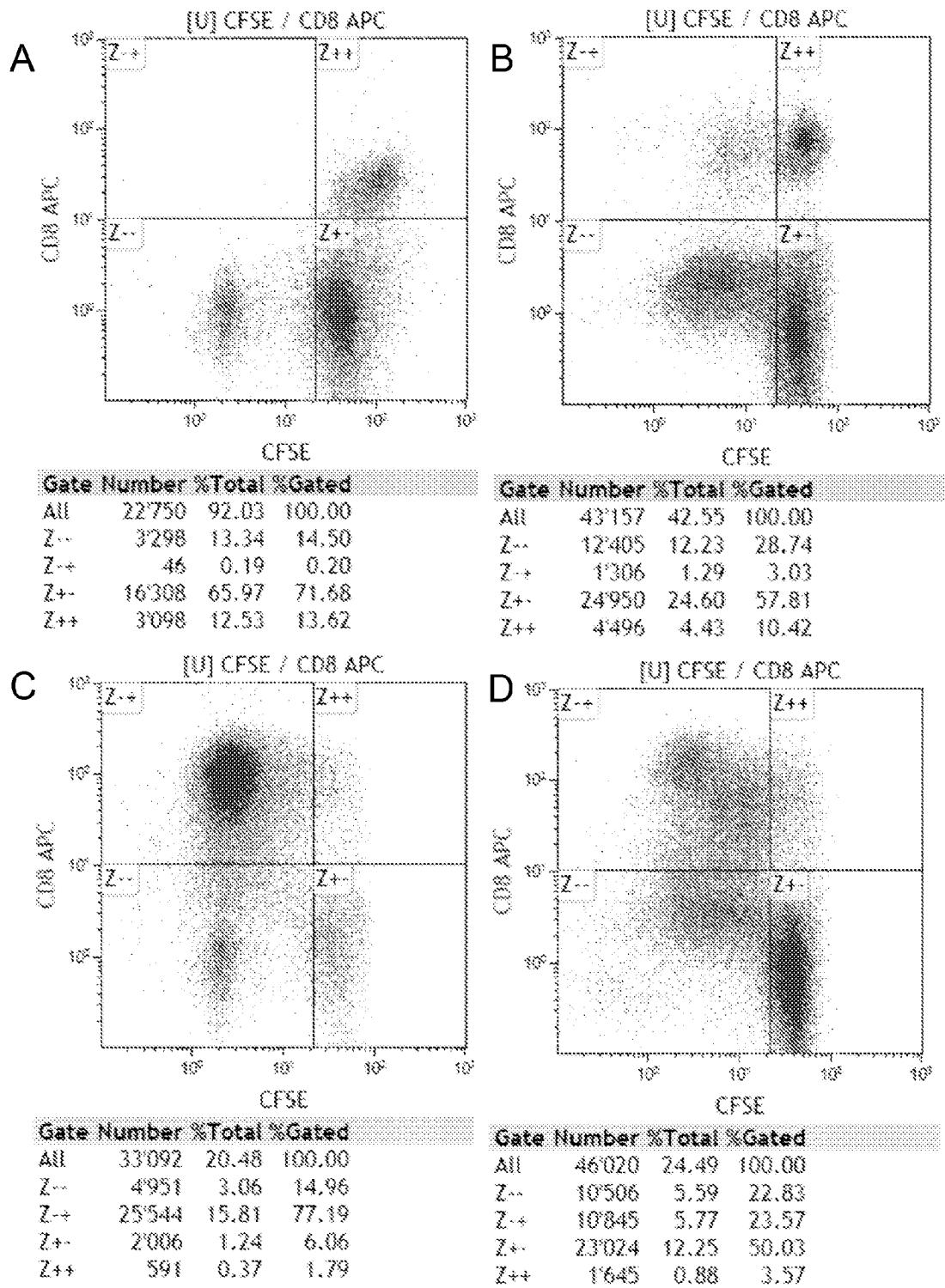
FIG. 1 shows results of MHC class I restricted presentation after loading into dendritic cells of CPP1-OVA and CPP2-OVA fusion polypeptides. Bone marrow derived dendritic cells were loaded during 4 h with 0.3 µM of the respective CPPs-OVA fusion polypeptides and matured overnight with LPS. After 5 days co-incubation with splenocytes from TCR transgenic mice OT1, correct MHC class I restricted presentation of the OVA epitope was assessed by CFSE dilution of the proliferating OVA-specific T cells. Negative controls with either T-cells only (A) or T-cells co-incubated with the matured bone marrow dendritic cells which were not pulsed with the fusion polypeptides (B); Positive controls with T-cells incubated with either peptides (C) or with peptides pulsed mature bone marrow derived dendritic cells (D); CPP1-OVA (E); CPP2-OVA (F).
Figure 1:
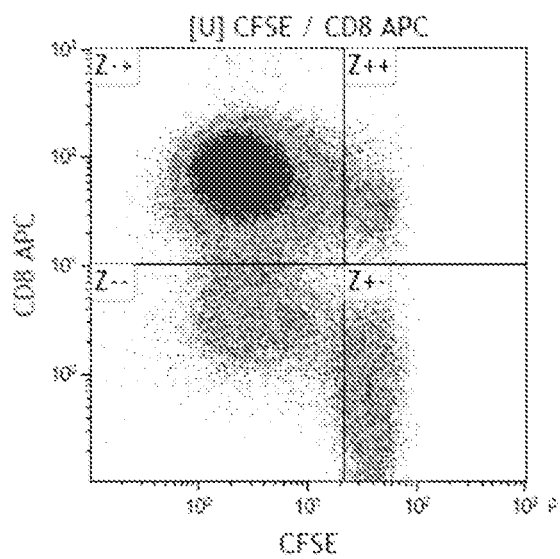
Figure 1:
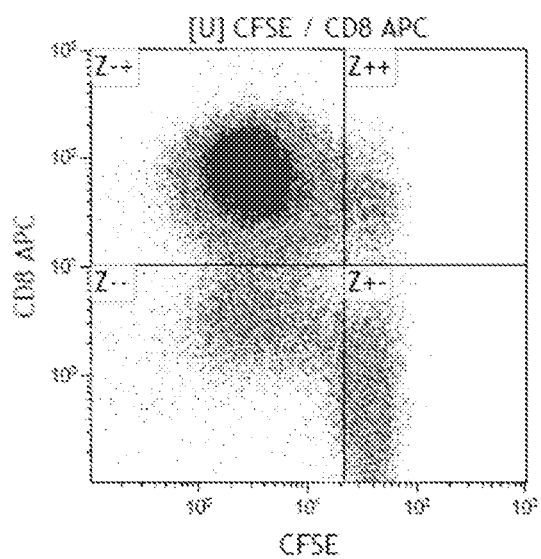

The terms "cell penetrating peptides" ("CPPs") are generally used to designate short peptides that are able to transport different types of cargo molecules across plasma membrane, and, thus, facilitate cellular uptake of various molecular cargoes (from nanosize particles to small chemical molecules, macromolecules, and large fragments of DNA). The "cargo" molecule is associated with the cell penetrating peptide either through chemical linkage via covalent bonds or through non-covalent interactions. Cell penetrating peptides typically have an amino acid composition that either contains a high relative abundance of positively charged amino acids such as lysine or arginine or have a sequence that contains an alternating pattern of polar/charged amino acids and non-polar, hydrophobic amino acids. These two types of structures are referred to as polycationic or amphipathic, respectively. Cell-Penetrating peptides are of different sizes, amino acid sequences, and charges but all CPPs have a common characteristic which is the ability to translocate the plasma membrane and facilitate the delivery of various molecular cargoes to the cytoplasm or to an organelle of a cell. At present, the theories of CPP translocation distinguish three main entry mechanisms: direct penetration in the membrane, endocytosis-mediated entry, and translocation through the formation of a transitory structure. CPP transduction is an area of ongoing research. Cell-penetrating peptides have found numerous applications in medicine as drug delivery agents in the treatment of different diseases including cancer and virus inhibitors, as well as contrast agents for cell labeling and imaging.

The "cargo molecule" designates herewith the molecule, linked to a cell penetrating peptide by covalent or non-covalent binding, the cellular internalization of which is facilitated or enabled by the presence of said cell penetrating peptide. In the present invention, "cargo molecules" includes peptides, proteins, polysaccharides, lipids, combinations thereof including lipoproteins and glycolipids, nucleic acids (e.g. DNA, siRNA, shRNA, antisense oligonucleotides, decoy DNA, plasmid), small molecule drugs (e.g. cyclosporine A, paclitaxel, doxorubicin, methotrexate, 5-aminolevulinic acid), imaging agents (e.g. fluorophore, quantum dots (QDs), radioactive tracers, metal chelates such as gadolinium ($Gd^{3+}$) low-molecular-weight chelates, superparamagnetic iron oxide (SPIO)). It is understood that, when the cargo molecule is a peptide, polypeptide or protein, it can comprise one or more peptides, polypeptides or proteins linked together. Also, when the cargo molecule is a nucleic acid, said nucleic acid can comprise one or more nucleic acids where each one encodes one peptide or polypeptide. Also the cargo molecule can be a combination of a protein, a lipid, and/or a polysaccharide including lipoproteins and glycolipids.

The terms "peptide", "polypeptide", "protein" and variations of these terms refer to peptide, oligopeptide, oligomer or protein including fusion protein, respectively, comprising at least two amino acids joined to each other by a normal or modified peptide bond, such as in the cases of the isosteric peptides, for example. These terms also include herewith "peptidomimetics" which are defined as peptide analogs containing non-peptidic structural elements, which peptides are capable of mimicking or antagonizing the biological action(s) of a natural parent peptide. A peptidomimetic lacks classical peptide characteristics such as enzymatically scissile peptide bonds. A peptide or polypeptide can be composed of amino acids other than the 20 amino acids defined by the genetic code. It can be composed of L-amino acids and/or D-amino acids. A peptide or polypeptide can equally be composed of amino acids modified by natural processes, such as post-translational maturation processes or by chemical processes, which are well known to a person skilled in the art. Such modifications are fully detailed in the literature. These modifications can appear anywhere in the polypeptide: in the peptide skeleton, in the amino acid chain or even at the carboxy- or amino-terminal ends. A peptide or polypeptide can be branched following an ubiquitination or be cyclic with or without branching. This type of modification can be the result of natural or synthetic post-translational processes that are well known to a person skilled in the art. For example, peptide or polypeptide modifications can include acetylation, acylation, ADP-ribosylation, amidation, covalent fixation of a nucleotide or of a nucleotide derivative, covalent fixation of a lipid or of a lipidic derivative, the covalent fixation of a phosphatidylinositol, covalent or non-covalent cross-linking, cyclization, disulfide bond formation, demethylation, glycosylation including pegylation, hydroxylation, iodization, methylation, myristoylation, oxidation, proteolytic processes, phosphorylation, prenylation, racemization, seneloylation, sulfatation, amino acid addition such as arginylation or ubiquitination. Such modifications are fully detailed in the literature (*Proteins Structure and Molecular Properties* (1993) 2nd Ed., T. E. Creighton, New York; *Post-translational Covalent Modifications of Proteins* (1983) B. C. Johnson, Ed., Academic Press, New York; Seifter et al. (1990) *Analysis for protein modifications and nonprotein cofactors, Meth. Enzymol.* 182: 626-646 and Rattan et al., (1992) *Protein Synthesis: Post-translational Modifications and Aging, Ann NY Acad Sci*, 663: 48-62).

The terms "cellular internalization" of the cargo molecule linked to the cell penetrating peptide generally means transport of the cargo molecule across the plasma membrane and thus entry of the cargo molecule into the cell. Depending on the particular case, the cargo molecule can, then, be released in the cytoplasm, directed to an intracellular organelle, or further presented at the cell surface.

The term "ZEBRA" (also known as Zta, Z, EB1, or BZLF1) generally means the basic-leucine zipper (bZIP) transcriptional activator of the Epstein-Barr virus (EBV). The minimal domain of ZEBRA, which exhibits cell penetrating properties, has been identified as spanning from residue 170 to residue 220 of ZEBRA. The amino acid sequence of ZEBRA is disclosed under NCBI accession number YP_401673 and comprises 245 amino acids represented in SEQ ID NO: 23.

The term "epitope", also known as "antigenic determinant", is the part of an antigen that is recognized by the immune system, specifically by antibodies, B cells, or T cells. In the present application, the term "epitope" is mainly used to designate T cell epitopes, which are presented on the surface of an antigen-presenting cell, where they are bound to Major Histocompatibility Complex (MHC). T cell epitopes presented by MHC class I molecules are typically, but not exclusively, peptides between 8 and 11 amino acids in length, whereas MHC class II molecules present longer peptides, generally, but not exclusively, between 12 and 25 amino acids in length.

The terms "CD4$^+$ epitope" or "CD4$^+$-restricted epitope" designates, herewith, an epitope recognized by a CD4$^+$ T cell, said epitope consisting of an antigen fragment lying in the groove of a MHC class II molecule.

The terms "CD8$^+$ epitope" or "CD8$^+$-restricted epitope" designates, herewith, an epitope recognized by a CD8$^+$ T cell, said epitope consisting of an antigen fragment lying in the groove of a MHC class I molecule.

The terms "epitope presentation in the MHC class I context" refer to a CD8$^+$ epitope lying in the groove of a MHC class I molecule at the surface of a cell.

The terms "epitope presentation in the MHC class II context" refer to a CD4$^+$ epitope lying in the groove of a MHC class II molecule at the surface of a cell.

The terms "epitope presentation in the CDI context" refer to a lipidic epitope lying in the groove of a cluster of differentiation 1 molecule at the surface of a cell.

"MHC class I" designates one of the two primary classes of the Major Histocompatibility Complex molecules. The MHC class I (also noted "MHC I") molecules are found on every nucleated cell of the body. The function of MHC class I is to display an epitope to cytotoxic cells (CTLs). In humans, MHC class I molecules consist of two polypeptide chains, α- and β2-microglobulin (b2m). Only the α chain is polymorphic and encoded by a HLA gene, while the b2m subunit is not polymorphic and encoded by the Beta-2 microglobulin gene.

"MHC class II" designates the other primary class of the Major Histocompatibility Complex molecules. The MHC class II (also noted "MHC II") molecules are found only on a few specialized cell types, including macrophages, dendritic cells and B cells, all of which are dedicated antigen-presenting cells (APCs).

"Tumor epitope" means, herewith, an epitope from a tumor-associated antigen or from a tumor-specific antigen. For instance, tumor epitopes include glioma epitopes.

"Pathogen epitope" means, herewith, an epitope from an antigenic protein, an antigenic polysaccharide, an antigenic lipid, an antigenic lipoprotein or an antigenic glycolipid from a pathogen including viruses, bacteria, fungi, protozoa and multicellular parasites. Antigenic proteins, polysaccharides, lipids, lipoproteins or glycolipids from pathogens include, herewith, proteins, polysaccharides, lipids, lipoproteins and glycolipids, respectively, from pathogens responsible of diseases which can be a target for vaccination including, for instance, Amoebiasis, Anthrax, Buruli Ulcer (*Mycobacterium ulcerans*), Caliciviruses associated diarrhoea, Campylobacter diarrhoea, Cervical Cancer (Human papillomavirus), *Chlamydia trachomatis* associated genital diseases, Cholera, Crimean-Congo haemorrhagic fever, Dengue Fever, Diptheria, Ebola haemorrhagic fever, Enterotoxigenic *Escherichia coli* (ETEC) diarrhoea, Gastric Cancer (*Helicobacter pylori*), Gonorrhea, Group A Streptococcus associated diseases, Group B Streptococcus associated diseases, *Haemophilus influenzae* B pneumonia and invasive disease, Hepatitis A, Hepatitis B, Hepatitis C, Hepatitis E diarrhoea, Herpes simplex type 2 genital ulcers, HIV/AIDS, Hookworm Disease, Influenza, Japanese encephalitis, Lassa Fever, Leishmaniasis, Leptospirosi, Liver cancer (Hepatitis B), Liver Cancer (Hepatitis C), Lyme Disease, Malaria, Marburg haemorrhagic fever, Measles, Mumps, Nasopharyngeal cancer (Epstein-Barr virus), *Neisseria meningitidis* Meningitis, Parainfluenza associated pneumonia, Pertussis, Plague, Poliomyelitis, Rabies, Respiratory syncytial virus (RSV) pneumonia, Rift Valley fever, Rotavirus diarrhoea, Rubella, Schistosomiasis, Severe Acute Respiratory Syndrome (SARS), Shigellosis, Smallpox, *Staphylococcus aureus* associated diseases, Stomach Cancer (*Helicobacter pylori*), *Streptococcus pneumoniae* and invasive disease, Tetanus, Tick-borne encephalitis, Trachoma, Tuberculosis, Tularaemia, Typhoid fever, West-Nile virus associated disease, Yellow fever.

The term "small inhibitory nucleic acids" (siNAs) refers to short nucleic acids used in strategies targeting mRNA recognition and its downregulation based on their antisense action. This term covers antisense oligonucleotides, catalytic nucleic acids such as ribozymes and deoxyribozymes, as well as small interfering RNAs (siRNAs).

The term "siRNA" refers to small interfering RNA which are single or double stranded RNA (about 19-23 nucleotides) able to knock down or silence a targeted mRNA from a target gene. Artificial siRNAs can be either chemically synthesized as oligonucleotides or cloned into a plasmid or a virus vector (adenovirus, retrovirus or lentivirus) as short hairpin RNAs (shRNAs) to generate a transient or stable transfection in any type of cells (Martin et al., 2007, *Ann. Rev. Genomics Hum. Genet.*, 8:81-108; Kolfschoten et al., 2007, *Nat. Clin. Pract. Endocrinol. Metab.*, 3(12):827-34; Huang et al., 2008, *Expert. Opin. Ther. Targets*, 12(5), 637-645).

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject who may be predisposed to the disease but has not yet been diagnosed as having it such as a preventive early asymptomatic intervention; (b) inhibiting the disease, i.e., arresting its development; or relieving the disease, i.e., causing regression of the disease and/or its symptoms or conditions such as improvement or remediation of damage. In particular, the methods, uses, formulations and compositions according to the invention are useful in the treatment of cancers or infectious diseases and/or in the prevention of evolution of cancers into an advanced or metastatic stage in patients with early stage cancer, thereby improving the staging of the cancer. When applied to cancers, prevention of a disease or disorder includes the prevention of the appearance or development of a cancer in an individual identified as at risk of developing said cancer, for instance due to past occurrence of said cancer in the circle of the individual's relatives, and prevention of infection with tumor promoting pathogens such as, for example, Epstein-Barr virus (EBV), Human papillomavirus (HPV), Hepatitis B virus (HBV), Hepatitis C virus (HCV), Human Herpes virus 8 (HHV8), human T-cell leukemia virus type 1 (HTLV-1), Merkel cell polyomavirus (MCV) and *Helicobacter pylori*. Also covered by the terms "prevention/treatment" of a cancer is the stabilization of an already diagnosed cancer in an individual. By "stabilization", it is meant the prevention of evolution of cancer into advanced or metastatic stage in patients with early stage cancer.

The term "subject" as used herein refers to mammals. For example, mammals contemplated by the present invention include human, primates, domesticated animals such as cattle, sheep, pigs, horses, laboratory rodents and the like.

The term "effective amount" as used herein refers to an amount of at least one cell penetrating peptide, complex comprising said cell penetrating peptide and a cargo molecule, cells loaded with said complex, composition or pharmaceutical formulation thereof according to the invention, that elicits the biological or medicinal response in a tissue, system, animal or human that is being sought. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active polypeptide sufficient to reduce the progression of the disease, notably to reduce or inhibit the tumor growth or infection and thereby elicit the response being sought, in particular such response could be an immune response directed against the epitopes comprised in the cargo molecule (i.e. an "inhibition effective amount").

The term "efficacy" of a treatment according to the invention can be measured based on changes in the course of disease in response to a use or a method according to the invention. For example, the efficacy of a treatment of cancer can be measured by a reduction of tumor volume, and/or an increase of progression free survival time, and/or a decreased risk of relapse post-resection for primary cancer. More specifically for cancer treated by immunotherapy, assessment of efficacy can be by the spectrum of clinical patterns of antitumor response for immunotherapeutic agents through novel immune-related response criteria (irRC), which are adapted from Response Evaluation Criteria in Solid Tumors (RECIST) and World Health Organization (WHO) criteria (*J. Natl. Cancer Inst.* 2010, 102(18): 1388-1397). The efficacy of prevention of infectious disease is ultimately assessed by epidemiological studies in human populations, which often correlates with titres of neutralizing antibodies in sera, and induction of multifunctional pathogen specific T cell responses. Preclinical assessment can include resistance to infection after challenge with infectious pathogen. Treatment of an infectious disease can be measured by inhibition of the pathogen's growth or elimination of the pathogen (and, thus, absence of detection of the pathogen), correlating with pathogen specific antibodies and/or T cell immune responses.

The term "pharmaceutical formulation" refers to preparations which are in such a form as to permit biological activity of the active ingredient(s) to be unequivocally effective and which contain no additional component which would be toxic to subjects to which the said formulation would be administered.

Cell Penetrating Peptides and Complexes According to the Invention

A first aspect of the invention relates to a cell penetrating peptide characterized in that:
  a) the length of the amino acid sequence of said peptide is comprised between 15 and 30 amino acids in total, such as 15, 16, 17, 18, 19, 20, 21, 22, 23, 24, 25, 26, 27, 28, 29, or 30 amino acids in total; and
  b) said peptide has an amino acid sequence comprising a fragment of the minimal domain of ZEBRA, said minimal domain extending from residue 170 to residue 220 of ZEBRA (SEQ ID NO: 23), wherein, optionally, 1, 2, 3, 4, or 5 amino acids have been substituted, deleted, and/or added without aborting said peptide's cell penetrating ability;
  or a variant of said peptide comprising an amino acid sequence having at least one conservatively substituted amino acid compared to said peptide's amino acid sequence.

Cell penetrating ability, or internalization, of the cell penetrating peptide or complex comprising said cell penetrating peptide, according to the invention can be checked by standard methods known to one skilled in the art, including flow cytometry or fluorescence microscopy of live and fixed cells, immunocytochemistry of cells transduced with said peptide or complex, and Western blot.

In an advantageous embodiment, the variants or fragments of the cell penetrating peptide according to the invention further retain said peptide's ability to present a proteic cargo molecule such as epitopes at the surface of a cell, such as an antigen-presenting cell, in the context of MHC class I and/or MHC class II molecules.

The ability of a cell penetrating peptide or complex comprising said cell penetrating peptide to present a proteic cargo molecule such as epitopes at the surface of a cell in the context of MHC class I and/or MHC class II molecules can be checked by standard methods known to one skilled in the art, including capacity to stimulate proliferation and/or function of MHC-restricted $CD4^+$ or $CD8^+$ T cells with specificity for these epitopes.

In a particular embodiment, the cell penetrating peptide according to the invention is not SEQ ID NO: 13.

In a particular embodiment, the cell penetrating peptide according to the invention is not SEQ ID NO: 14.

In another particular embodiment, the cell penetrating peptide according to the invention comprises a Cys (C) substituted into a Ser (S), at the equivalent of position 189 relative to ZEBRA amino acid sequence of SEQ ID NO: 23.

In one embodiment, the invention relates to a cell penetrating peptide characterized in that:
  a) said peptide has an amino acid sequence having a length of at least 15, and at most 30 amino acids; and
  b) said peptide has an amino acid sequence comprising:
    (i) SEQ ID NO: 1, or
    (ii) an amino acid sequence identical to SEQ ID NO: 1 except that 1, 2, 3, 4, or 5 amino acids are substituted, deleted, and/or added without aborting said peptide's cell penetrating ability;

or a variant of said peptide comprising an amino acid sequence having at least one conservatively substituted amino acid compared to said peptide's amino acid sequence.

According to one aspect of the invention, the cell penetrating peptide comprises an amino acid sequence having at least one conservatively substituted amino acid compared to the referenced sequence, meaning that a given amino acid residue is replaced by a residue having similar physiochemical characteristics.

Generally, substitutions for one or more amino acids present in the referenced amino acid sequence should be made conservatively. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity properties, are well known (Kyte and Doolittle, 1982, *J. Mol. Biol.* 157(1):105-132). Substitutions of one or more L-amino acids with one or more D-amino acids are to be considered as conservative substitutions in the context of the present invention. Exemplary amino acid substitutions are presented in Table 1 below:

TABLE 1

| Original residues | Examples of substitutions |
|---|---|
| Ala (A) | Val, Leu, Ile, Gly |
| Arg (R) | His, Lys |
| Asn (N) | Gln |
| Asp (D) | Glu |
| Cys (C) | Ser |
| Gln (Q) | Asn |
| Glu (E) | Asp |
| Gly (G) | Pro, Ala |
| His (H) | Lys, Arg |
| Ile (I) | Leu, Val, Met, Ala, Phe |
| Leu (L) | Ile, Val, Met, Ala, Phe |
| Lys (K) | Arg, His |
| Met (M) | Leu, Ile, Phe |
| Phe (F) | Leu, Val, Ile, Tyr, Trp, Met |
| Pro (P) | Ala, Gly |
| Ser (S) | Thr |
| Thr (T) | Ser |
| Trp (W) | Tyr, Phe |
| Tyr (Y) | Trp, Phe |
| Val (V) | Ile, Met, Leu, Phe, Ala |

Thus, in another aspect, the cell penetrating peptide according to the invention is characterized in that:
a) said peptide has an amino acid sequence having a length of at least 15, and at most 30 amino acids; and
b) said peptide has an amino acid sequence comprising SEQ ID NO: 6 with 0, 1, 2, 3, 4, or 5 amino acids which are substituted, deleted, and/or added without aborting said peptide's cell penetrating ability, wherein
$X_1$ is K, R, or H
$X_2$ is R, K, or H
$X_3$ is Y, W, or F
$X_4$ is K, R, or H
$X_5$ is N or Q
$X_6$ is R, K, or H
$X_7$ is V, I, M, L, F, or A
$X_8$ is A, V, L, I, or G
$X_9$ is S or T
$X_{10}$ is R, K, or H
$X_{11}$ is K, R, or H
$X_{13}$ is R, K, or H
$X_{14}$ is A, V, L, I, or G
$X_{15}$ is K, R, or H
$X_{16}$ is F, L, V, I, Y, W, or M
$X_{17}$ is K, R, or H.

In a particular embodiment, the cell penetrating peptide according to the invention is as generically defined above by reference to SEQ ID NO: 6, wherein $X_1$ is K.

In a particular embodiment, the cell penetrating peptide according to the invention is as generically defined above by reference to SEQ ID NO: 6, wherein $X_2$ is R.

In a particular embodiment, the cell penetrating peptide according to the invention is as generically defined above by reference to SEQ ID NO: 6, wherein $X_3$ is Y.

In a particular embodiment, the cell penetrating peptide according to the invention is as generically defined above by reference to SEQ ID NO: 6, wherein $X_4$ is K.

In a particular embodiment, the cell penetrating peptide according to the invention is as generically defined above by reference to SEQ ID NO: 6, wherein $X_5$ is N.

In a particular embodiment, the cell penetrating peptide according to the invention is as generically defined above by reference to SEQ ID NO: 6, wherein $X_6$ is R.

In a particular embodiment, the cell penetrating peptide according to the invention is as generically defined above by reference to SEQ ID NO: 6, wherein $X_7$ is V.

In a particular embodiment, the cell penetrating peptide according to the invention is as generically defined above by reference to SEQ ID NO: 6, wherein $X_8$ is A.

In a particular embodiment, the cell penetrating peptide according to the invention is as generically defined above by reference to SEQ ID NO: 6, wherein $X_9$ is S.

In a particular embodiment, the cell penetrating peptide according to the invention is as generically defined above by reference to SEQ ID NO: 6, wherein $X_{10}$ is R.

In a particular embodiment, the cell penetrating peptide according to the invention is as generically defined above by reference to SEQ ID NO: 6, wherein $X_{11}$ is K.

In a particular embodiment, the cell penetrating peptide according to the invention is as generically defined above by reference to SEQ ID NO: 6, wherein $X_{13}$ is R.

In a particular embodiment, the cell penetrating peptide according to the invention is as generically defined above by reference to SEQ ID NO: 6, wherein $X_{14}$ is A.

In a particular embodiment, the cell penetrating peptide according to the invention is as generically defined above by reference to SEQ ID NO: 6, wherein $X_{15}$ is K.

In a particular embodiment, the cell penetrating peptide according to the invention is as generically defined above by reference to SEQ ID NO: 6, wherein $X_{16}$ is F.

In a particular embodiment, the cell penetrating peptide according to the invention is as generically defined above by reference to SEQ ID NO: 6, wherein $X_{17}$ is K.

In a particular embodiment, the cell penetrating peptide according to the invention is as generically defined above by reference to SEQ ID NO: 6, wherein the amino acid at position equivalent to position 12 relative to SEQ ID NO: 6 is a Ser (S).

In a more particular aspect, said cell penetrating peptide comprises an amino acid sequence comprising SEQ ID NO: 7, wherein
$X_1$ is K or R
$X_2$ is R or K
$X_3$ is Y, W, or F
$X_4$ is K or R
$X_5$ is N or Q
$X_6$ is R or K
$X_7$ is V, I, M or L $X_8$ is A or G
$X_9$ is S or T
$X_{10}$ is R or K
$X_{11}$ is K or R
$X_{13}$ is R or K
$X_{14}$ is A or G
$X_{15}$ is K or R
$X_{16}$ is F, Y, or W
$X_{17}$ is K or R.

In particular, the cell penetrating peptide according to the invention has an amino acid sequence comprising or consisting of SEQ ID NO: 1 or SEQ ID NO: 2.

In another embodiment, the cell penetrating peptide according to the invention has an amino acid sequence comprising or consisting of SEQ ID NO: 1.

In another embodiment, the invention relates to a cell penetrating peptide comprising or consisting of amino acid sequence SEQ ID NO: 8.

In another particular embodiment, said cell penetrating peptide comprises or consists of amino acid sequence SEQ ID NO: 9.

In another embodiment, the invention relates to a cell penetrating peptide comprising or consisting of amino acid sequence SEQ ID NO: 10.

It will be understood by one skilled in the art that the primary amino acid sequence of the cell penetrating peptide of the invention may further be post-translationally modified, such as by glycosylation or phosphorylation, without departing from the invention.

In a further embodiment, the cell penetrating peptide according to the invention optionally further comprises, in addition to its amino acid sequence as described above, any one of, or any combination of:
(i) a nuclear localization signal (NLS). Such signals are well known to the skilled person and are described in Nair et al. (2003, *Nucleic Acids Res*. 31(1): 397-399)
(ii) a targeting peptide, including tumor homing peptides such as those described in Kapoor et al. (2012, *PLoS ONE* 7(4): e35187) and listed in http://crdd.osdd.net/raghava/tumorhope/general.php?

In another embodiment, the cell penetrating peptide according to the invention is linked to a cargo molecule and facilitates the cellular internalization of said cargo molecule.

Thus, another aspect of the invention relates to a complex comprising a cell penetrating peptide according to the invention and a cargo molecule.

The cargo molecule can either be linked to the C-terminal part or to the N-terminal part of the cell penetrating peptide according to the invention.

In a particular embodiment, the cargo molecule that is linked to the cell penetrating peptide according to the invention or that is comprised in the complex according to the invention can be selected from the group consisting of: (i) a peptide, a polypeptide or a protein, (ii) a polysaccharide, (iii) a lipid, (iv) a lipoprotein, (v) a glycolipid, (vi) a nucleic acid, (vii) a small molecule drug or toxin, and (viii) an imaging or contrast agent.

It is understood that the cargo molecule can comprise more than one peptide, polypeptide, or protein, more than one polysaccharide, more than one lipid, more than one lipoprotein, more than one glycolipid, more than one nucleic acid, more than one small molecule drug or toxin, more than one imaging or contrast agent, or a combination thereof.

In a further embodiment, the cargo molecule that is linked to the cell penetrating peptide according to the invention or that is comprised in the complex according to the invention is selected among pathogen epitopes and/or tumor epitopes.

One embodiment concerns a complex comprising a cell penetrating peptide according to the invention and a cargo molecule, wherein said cargo molecule is a peptide, polypeptide, or protein.

Examples of cargo molecules of peptidic, polypeptidic, or proteic nature useful in the invention, include epitopes, antibodies, antibody fragments, therapeutic proteins, transcription factors, transactivators and decoy peptides. For instance, the cargo molecule can comprise $CD4^+$ epitope(s) and/or $CD8^+$ epitopes corresponding to antigenic determinant(s) of a tumor-associated antigen, a tumor-specific antigen, or an antigenic protein from a pathogen. The $CD4^+$ epitopes comprised in the polypeptide of the invention generally, and preferably, consist of about 12-25 amino acids. They can also consist of about 8-25 amino acids or about 6-100 amino acids. The $CD8^+$ epitopes comprised in the polypeptide of the invention generally, and preferably, consist of about 8-11 amino acids. They may also consist of about 8-15 amino acids or about 6-100 amino acids.

In a specific embodiment, the complex according to the invention comprises a cargo molecule selected from epitopes, antibodies, antibody fragments, therapeutic proteins, transcription factors, transactivators and decoy peptides.

In a more specific embodiment, the complex according to the invention comprises a cargo molecule comprising one or more epitopes, which can be tumor epitopes and/or pathogen epitopes as defined herewith.

In a specific embodiment, the complex according to the invention comprises a cargo molecule comprising epitope(s) from a tumor-associated antigen, a tumor-specific antigen, and/or an antigenic protein from a pathogen, including viral, bacterial, fungal, protozoal and multicellular parasitic antigenic protein.

In a particular illustration of the invention, said epitopes will be presented at the cell surface in an MHC class I and/or MHC class II context.

Examples of cargo molecules within the category of peptide, polypeptide or protein include a combination of multiple glioma epitopes such as those described in Novellino et al. (2005, *Cancer Immunol Immunother*, 54(3):187-207), Vigneron et al. (2013, *Cancer Immun*.13:15).

In another aspect of the invention, all of said glioma epitopes are not linked to the same cell penetrating peptide which would form a single complex according to the invention, but are linked, either individually or by groups of at least 2 epitopes, to independent cell penetrating peptides according to the invention, forming at least 2 distinct complexes according to the invention.

In an advantageous embodiment, the complex according to the invention comprises a cell penetrating peptide and epitopes, and allows the transport and presentation of said epitopes at the cell surface of antigen presenting cells in an MHC class I and MHC class II context, and is, thus, useful in vaccination and immunotherapy.

In a particular aspect, the complex according to the invention comprises a spacer or linker which are non-immunologic cleavable moieties linking the cell penetrating peptide and the cargo molecule, and/or linking successive epitopes comprised in a peptidic, polypeptidic or proteic cargo molecule, and/or linking successive cargo molecules, and/or be placed at the C-terminal part of the cargo molecule.

Said spacer may be peptidic or non-peptidic, the linkage between two components of the complex according to the invention may be a covalent linkage or a non-covalent linkage.

A peptidic spacer can consist of about 1, 2, 3, 4, 5, 6, 7, 8, 9, or 10 amino acids, for instance. The amino acid sequence of the peptidic spacer may be identical to that of the N-terminal or C-terminal flanking region of the cargo molecule or of an epitope of said cargo molecule. Alternatively a peptidic spacer can consist of non-natural amino acid sequences such as an amino acid sequence resulting from conservative amino acid substitutions of said natural flanking regions or sequences of known cleavage sites for proteases such as the enterokinase target site (amino acid sequence DDDK, SEQ ID NO: 15), factor Xa target site (amino acid sequence IEDGR, SEQ ID NO: 16), thrombin target site (amino acid sequence LVPRGS, SEQ ID NO: 17), protease TEV target site (amino acid sequence ENLYFQG, SEQ ID NO: 18), PreScission protease target site (amino acid sequence LEVLFQGP, SEQ ID NO: 19), polycationic amino acids, e.g. poly K, furin target site (amino acid sequence RX(R/K)R, SEQ ID NO: 20). In particular embodiment, the peptidic spacer does not contain any Cys (C) residues.

A non-peptidic spacer can include esters, thioesters or di-sulfides.

In a particular aspect, the complex according to the invention comprises a spacer or linker, in particular a peptidic spacer placed between the cell penetrating peptide sequence and the peptidic, polypeptidic, or proteic cargo. This peptidic spacer can be chosen by one skilled in the art so that it may be cut by the cell machinery once the complex comprising the cell penetrating peptide and the cargo molecule has been internalized, thus, liberating the cargo free of cell penetrating peptide within the cell, an organelle, or at the cell surface.

In a more particular aspect, said spacer linking the cell penetrating peptide and the peptidic, polypeptidic, or proteic cargo molecule, or an adjacent epitope from the peptidic, polypeptidic, or proteic cargo molecule, may consist of about 1, 2, 3, 4, or 5 amino acids, which correspond to about 1, 2, 3, 4, or 5 amino acids of the region flanking said cargo molecule or adjacent epitope.

When the cargo molecule comprises several epitopes, it will be clear for one skilled in the art that each of the epitopes comprised in the complex of the invention can be either directly linked to each other or linked via spacers or linkers such as a peptidic spacer consisting of a few amino acids. Alternatively, when the cargo molecule comprises several epitopes, it is also possible that some epitopes comprised in the complex of the invention are directly linked to each other and some other epitopes are linked via spacers or linkers such as a peptidic spacer consisting of a few amino acids.

In a specific aspect of the invention, two successive epitopes comprised in the peptidic, polypeptidic, or proteic cargo molecule of the invention are linked to each other by spacers consisting of the natural flanking regions of said epitopes. According to one embodiment, the spacer used to link a first epitope to a second epitope consists of up to about 8 amino acids corresponding to up to about 4 amino acids of the N-terminal or C-terminal flanking region of the first epitope, followed by up to about 4 amino acids of the N-terminal or C-terminal flanking region of the second epitope. In an illustration of the present invention, the spacer used to link a first epitope ("epitope 1") to a second epitope ("epitope 2") consists of about 8 amino acids corresponding to any possible combination ranging from: 0 flanking amino acid of epitope 1 and 8 flanking amino acids of epitope 2, to 8 flanking amino acids of epitope 1 and 0 flanking amino acid of epitope 2, i.e. including 1 flanking amino acid of epitope 1 and 7 flanking amino acids of epitope 2, 2 flanking amino acid of epitope 1 and 6 flanking amino acids of epitope 2, 3 flanking amino acid of epitope 1 and 5 flanking amino acids of epitope 2, 4 flanking amino acid of epitope 1 and 4 flanking amino acids of epitope 2, 5 flanking amino acid of epitope 1 and 3 flanking amino acids of epitope 2, 6 flanking amino acid of epitope 1 and 2 flanking amino acids of epitope 2, 7 flanking amino acid of epitope 1 and 1 flanking amino acid of epitope 2, 8 flanking amino acid of epitope 1 and 0 flanking amino acids of epitope 2. It will be understood that the total of 8 amino acids constituting a spacer linking two successive epitopes is not an absolute value and the spacer could also be composed of a total of, for instance, 3 amino acids, 4 amino acids, 5 amino acids, 6 amino acids, 7 amino acids, 9 amino acids or 10 amino acids. Similarly, equivalent combinations as mentioned above are also an illustration of the invention in the situation where a spacer has less or more than 8 amino acids.

In another particular illustration of the present invention, the spacer used to link a first epitope ("epitope 1") to a second epitope ("epitope 2") consists of about 4 amino acids, e.g. 1, 2, 3, 4, or 5 amino acids. More particularly, said spacer's amino acid sequence can correspond to the 4 amino acids of the N-terminal or C-terminal flanking region of epitope 1 or epitope 2.

A spacer as described above may also be placed at the C-terminal part of the last epitope comprised in the cargo molecule.

Examples of a peptidic spacer include the amino acid sequences EQLE (SEQ ID NO: 11) or TEWT (SEQ ID NO: 12) for instance or any conservative substitutions thereof.

Another embodiment concerns a complex comprising a cell penetrating peptide according to the invention and a cargo molecule, wherein said cargo molecule is a polysaccharide, a lipid, a lipoprotein, and/or a glycolipid, in particular a polysaccharidic, lipidic, lipoproteic, and/or glycolipidic epitope, which can be pathogen epitopes as defined herewith.

In a particular illustration, the complex according to the invention comprises a cargo molecule comprising polysaccharidic, lipidic, lipoproteic, and/or glycolipidic epitope(s) from an antigen from a pathogen, including viral, bacterial, fungal, protozoal and multicellular parasitic antigens.

In a particular illustration of the invention, said epitopes will be presented at the cell surface in an MHC class I and/or MHC class II context.

In another illustration of the invention, said lipidic epitopes will be presented at the cell surface in a CD1 (cluster of differentiation 1) context.

Another embodiment provides a complex comprising a cell penetrating peptide according to the invention and a cargo molecule, wherein said cargo molecule is a small molecule drug or toxin.

Examples of cargo molecules within the category of small molecule drugs or toxins useful in the invention include cyclosporine A, paclitaxel, doxorubicin, methotrexate, 5-aminolevulinic acid, diphtheria toxin, sunitinib and those molecules reviewed in *De wit Amer* (2010, *Neuro Oncol*, 12(3):304-16).

Still another embodiment provides a complex comprising a cell penetrating peptide according to the invention and a cargo molecule, wherein said cargo molecule is an imaging or contrast agent.

Examples of cargo molecules within the category of imaging or contrast agent useful in the invention include fluorophores, quantum dots (QDs), metal chelates such as gadolinium ($Gd^{3+}$) low-molecular-weight chelates and superparamagnetic iron oxide (SPIO), radioactive tracers.

Another embodiment provides a complex comprising a cell penetrating peptide according to the invention and a cargo molecule, wherein said cargo molecule is a nucleic acid.

Examples of nucleic acid cargo molecules useful in the invention include DNA, RNA, siRNA, shRNA, antisense oligonucleotides, decoy DNA, plasmids, microRNAs.

Another embodiment provides a complex comprising a cell penetrating peptide according to the invention and a cargo molecule, wherein said cargo molecule is a nucleic acid encoding a peptide, polypeptide, or protein, in particular encoding a peptide, polypeptide or protein comprising epitopes.

Examples of cargo molecules within the category of nucleic acids include a nucleic acid encoding the peptidic, polypeptidic or proteic cargo molecule according to the invention. A particular example is a nucleic acid encoding epitopes comprised in the peptidic, polypeptidic or proteic cargo molecule according to the invention. Another example is a nucleic acid encoding a combination of multiple glioma epitopes such as those described in Reardon et at (2013, *Expert Rev Vaccines*, 12(6): 597-615).

In another advantageous embodiment, the complex according to the invention comprises a cell penetrating peptide and a nucleic acid encoding epitopes, and allows the transport of said nucleic acid within the cell. The transduced nucleic acid can then be transcribed and translated to produce said epitopes within the cell which are, in turn, presented at the cell surface of antigen presenting cells in an MHC class I and MHC class II context. Such a complex is, thus, useful in vaccination and immunotherapy.

In one embodiment of the invention, the cargo molecule can be covalently or non-covalently linked to the cell penetrating peptide according to the invention, including by a peptidic spacer as described herewith.

The technics for linking the cell penetrating peptide according to the invention and the cargo molecule are well documented in the literature and can depend on the nature of the cargo molecule. For instance, linkages between the cargo molecule and the cell penetrating peptide can be achieved via cleavable disulphide linkages through total stepwise solid-phase synthesis or solution-phase or solid-phase fragment coupling, stable amide, thiazolidine, oxime and hydrazine linkage, disulphide linkage, stable thiomaleimide linkage, peptide bound (including peptide bounds between amino acids of a fusion protein), or electrostatic or hydrophobic interactions.

Polynucleotides Encoding the Peptides and Protein Complexes According to the Invention Another aspect of the invention relates to polynucleotides encoding the cell penetrating peptide or complex comprising a peptidic, polypeptidic or proteic cargo molecule, according to the invention.

In one embodiment, the invention relates to a nucleic acid encoding the cell penetrating peptide according to the invention or encoding a complex comprising said cell penetrating peptide covalently linked to a peptide, polypeptide or protein cargo molecule, possibly with peptidic spacer(s) as described herewith.

In a further embodiment, the invention relates to a nucleic acid encoding the cell penetrating peptide according to the invention or encoding a complex comprising said cell penetrating peptide covalently linked to a peptide, polypeptide or protein cargo molecule comprising at least one epitope, possibly with peptidic spacer(s) as described herewith.

In a still further embodiment, the invention relates to a nucleic acid encoding a peptide, polypeptide or protein cargo molecule according to the invention comprising at least one epitope.

Production and Purification of the Cell Penetrating Peptides and Complexes According to the Invention Another aspect of the invention provides a recombinant vector comprising a polynucleotide according to the invention.

Numerous expression systems can be used, including without limitation chromosomes, episomes, and derived viruses. More particularly, the recombinant vectors used can be derived from bacterial plasmids, transposons, yeast episomes, insertion elements, yeast chromosome elements, viruses such as baculovirus, papilloma viruses such as SV40, vaccinia viruses, adenoviruses, fox pox viruses, pseudorabies viruses, retroviruses.

These recombinant vectors can equally be cosmid or phagemid derivatives. The nucleotide sequence can be inserted in the recombinant expression vector by methods well known to a person skilled in the art such as, for example, those that are described in MOLECULAR CLONING: A LABORATORY MANUAL, Sambrook et al., 4th Ed., Cold Spring Harbor Laboratory Press, Cold Spring Harbor, N.Y., 2001.

The recombinant vector can include nucleotide sequences that control the regulation of the polynucleotide expression as well as nucleotide sequences permitting the expression and the transcription of a polynucleotide of the invention and the translation of a polypeptide of the invention, these sequences being selected according to the host cells that are used.

Thus, for example, an appropriate secretion signal can be integrated in the recombinant vector so that the polypeptide, encoded by the polynucleotide of the invention, will be directed towards the lumen of the endoplasmic reticulum, towards the periplasmic space, on the membrane or towards the extracellular environment. The choice of an appropriate secretion signal may facilitate subsequent protein purification.

In a further embodiment, it is provided a host cell comprising a recombinant vector according to the invention.

The introduction of the recombinant vector in a host cell can be carried out according to methods that are well known to a person skilled in the art, such as those described in BASIC METHODS IN MOLECULAR BIOLOGY, Davis et al., 2nd ed., McGraw-Hill Professional Publishing, 1995, and MOLECULAR CLONING: A LABORATORY MANUAL, supra, such as transfection by calcium phosphate, transfection by DEAE dextran, transfection, microinjection, transfection by cationic lipids, electroporation, transduction or infection.

The host cell can be, for example, bacterial cells such as *E. coli*, cells of fungi such as yeast cells and cells of *Aspergillus, Streptomyces*, insect cells, Chinese Hamster Ovary cells (CHO), C127 mouse cell line, BHK cell line of Syrian hamster cells, Human Embryonic Kidney 293 (HEK 293) cells.

The host cells can be used, for example, to express a polypeptide of the invention. After purification by standard methods, the polypeptide of the invention can be used in a method described hereinafter.

It is a further embodiment of the invention to provide a method for preparing a cell penetrating peptide according to the invention or a complex comprising said cell penetrating peptide covalently linked to a peptide, polypeptide or protein cargo molecule, according to the invention, comprising cultivating a host cell as mentioned above in a culture medium and separating said cell penetrating peptide or complex from the culture medium or separating said cell penetrating peptide or complex from the host cell lysate after host cell lysis.

In another embodiment, the cell penetrating peptides and complexes according to the invention can be prepared by synthetic chemistry methods, such as solid-phase peptide synthesis. Purification of those peptides may be carried out by means of any technique known in the art for protein/peptide purification. Exemplary techniques include ion-exchange chromatography, hydrophobic interaction chromatography, and immunoaffinity methods.

It is a further embodiment of the invention to provide a method for preparing a cell penetrating peptide according to the invention comprising chemically synthesizing and purifying said peptide.

It is another embodiment of the invention to provide a method for preparing a complex according to the invention comprising a cell penetrating peptide covalently linked to a peptide, polypeptide or protein cargo molecule, as defined herewith, comprising chemically synthesizing and purifying a polypeptide which amino acid sequence comprises the amino acid sequence of said cell penetrating peptide and the amino acid sequence of said peptide, polypeptide or protein cargo molecule.

In another embodiment, the method according to the invention comprises synthesizing the cell penetrating peptide and the cargo molecule separately, and either mixing the purified peptides and cargo molecule or covalently linking said peptide and cargo molecule.

Cells Loaded with the Complexes According to the Invention

Another aspect of the invention relates to cells loaded with the complex according to the invention. In a particular embodiment, the cells are from the patient to be treated.

In a further embodiment, the cells are cells of the immune system such as antigen presenting cells or stem cells such as neural stem cells.

In one embodiment, it is provided antigen-presenting cells loaded with the complex according to the invention.

In a specific embodiment, the antigen presenting cells are selected among dendritic cells, macrophages and B-cells. Dendritic cells, in particular dendritic cells (conventional and plasmacytoid) from the patient to be treated, are preferred. Methods to extract antigen-presenting cells, in particular dendritic cells, from the patient are known to the skilled person. They include harvesting monocytes or hematopoietic stem cells from bone marrow, cord blood, or peripheral blood. They also include the use of embryonic stem (ES) cells and induced pluripotent stem cells (iPS). Antigen presenting cells, in particular dendritic cells or their precursors, can be enriched by methods including elutriation and magnetic bead based separation, which may involve enrichment for CD14$^+$ precursor cells.

Methods to load the complex of the invention into the cells, in particular into the above-mentioned antigen presenting cells and further prepare such cells before administration to the patient are known to one skilled in the art. Preparation of dendritic cells can include their culture or differentiation using cytokines that may include GM-CSF and IL-4. Dendritic cell lines may also be employed. Loading of the complex of the invention into the cells, in particular into the dendritic cells, can involve co-incubation of the complex of the invention with the cells in culture, making use of the intrinsic properties of the cell penetrating peptide of the invention (i.e. its internalization ability).

Further culture of the dendritic cells thus loaded to induce efficient maturation can include addition of cytokines including IL-1β, IL-6, TNFα, PGE2, IFNα, and adjuvants which may include poly-IC, poly-ICLC (i.e. a synthetic complex of carboxymethylcellulose, polyinosinic-polycytidylic acid, and poly-L-lysine double-stranded RNA), and other TLR (toll-like receptors) and NLR (nucleotide-binding oligomerization domain-like receptors) agonists.

A further aspect concerns imaging cells used for cell therapy, such as stem cells, dendritic cells, T cells or natural killer cells, loaded with the complex according to the invention wherein the cargo molecule is an imaging agent.

It is also an object of the invention to provide a method for preparing cells, in particular antigen presenting cells, loaded with the complex according to the invention as mentioned above, comprising transducing said cells with the complex of the invention, cultivating said cells in a culture medium and separating said cells from the culture medium.

In a particular embodiment, the cells are loaded with complex(es) comprising a cargo molecule wherein said cargo molecule is selected among (i) a peptide, polypeptide or protein or (ii) a nucleic acid.

In another embodiment of the invention, the cells loaded with complex(es) comprising epitopes according to the invention present said epitopes at the cell surface in an MHC class I and MHC class II contexts.

Compositions and Kits According to the Invention

The invention provides compositions comprising at least one component selected from:
 (i) a cell penetrating peptide of the invention,
 (ii) a complex of the invention,
 (iii) a nucleic acid of the invention,
 (iv) a vector of the invention,
 (v) a host cell of the invention, and
 (vi) a cell loaded with a complex according to the invention.

In a particular embodiment, the composition of the invention comprises more than one of the components under (i) to (vi).

In an illustration of the invention, the composition comprises at least two different peptides under (i), at least two different complexes under (ii), at least two different nucleic acids under (iii), at least two different vectors under (iv), at least two different host cells under (v), and/or at least two different cells under (vi).

In another illustration, the composition of the invention comprises at least two different complexes and/or at least two different nucleic acids according to the invention.

In particular, the composition of the invention can comprise more than one complex according to the invention, for instance at least two complexes wherein each complex comprises one or more cargo molecules and wherein said cargo molecules are different between the complexes.

In an illustration, the composition of the invention comprises at least 2 complexes, wherein each complex comprises one or more epitopes and wherein said epitopes are different between the complexes.

In another illustration, the composition of the invention comprises at least 2 complexes, wherein each complex comprises one or more nucleic acids encoding one or more epitopes and wherein said nucleic acids are different between the complexes.

The present invention also provides a complex or cells loaded with said complex, as described herewith, for use as a medicament, in particular as a vaccine.

In a particular embodiment, the present invention provides a complex or cells loaded with said complex, as described herewith, for use in the treatment of diseases or disorders including cancers, infectious diseases, autoimmunity disorders and transplant rejections.

In another embodiment, the present invention provides a complex or cells loaded with said complex, as described herewith, for use as an imaging or diagnostic composition.

The invention also provides an imaging composition or a diagnostic composition comprising a complex according to the invention or cells loaded with said complex, as described herewith.

The invention provides pharmaceutical compositions, in particular vaccine compositions, and methods for treating a subject, preferably a mammalian subject, and most preferably a human patient who is susceptible to, or suffering from a medical disorder, and in particular a disorder that can be treated by immunotherapy such as cancers, infectious diseases, autoimmunity disorders and transplant rejections.

Pharmaceutical compositions, in particular vaccine compositions, or formulations according to the invention may be administered as a pharmaceutical formulation which can contain a cell penetrating peptide or complex according to the invention in any form described herein.

Pharmaceutical compositions, in particular vaccine compositions, or formulations according to the invention may also be administered as a pharmaceutical formulation which can contain antigen presenting cells loaded with a complex according to the invention in any form described herein.

The compositions according to the invention, together with a conventionally employed adjuvant, immunomodulatory material, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous and intradermal) use by injection or continuous infusion. Injectable compositions are typically based upon injectable sterile saline or phosphate-buffered saline or other injectable carriers known in the art. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Examples of suitable adjuvants and/or immunomodulatory materials include MPL® (Corixa), aluminum-based minerals including aluminum compounds (generically called Alum), ASO1-4, MF59, CalciumPhosphate, Liposomes, Iscom, polyinosinic:polycytidylic acid (poly-IC), including its stabilized form poly-ICLC (Hiltonol), CpG oligodeoxynucleotides, Granulocyte-macrophage colony-stimulating factor (GM-CSF), lipopolysaccharide (LPS), Montanide, polylactide co-glycolide (PLG), Flagellin, Soap Bark tree saponins (QS21), amino alkyl glucosamide compounds (e.g. RC529), two component antibacterial peptides with synthetic oligodeoxynucleotides (e.g. IC31), Imiquimod, Resiquimod, Immunostimulatory sequences (ISS), monophosphoryl lipid A (MPLA), Fibroblast-stimulating lipopeptide (FSL1), and anti-CD40 antibodies.

Compositions of the invention may be liquid formulations including, but not limited to, aqueous or oily suspensions, solutions, emulsions, syrups, and elixirs. The compositions may also be formulated as a dry product for reconstitution with water or other suitable vehicle before use. Such liquid preparations may contain additives including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethyl cellulose, carboxymethyl cellulose, aluminum stearate gel, and hydrogenated edible fats. Emulsifying agents include, but are not limited to, lecithin, sorbitan monooleate, and acacia. Preservatives include, but are not limited to, methyl or propyl p-hydroxybenzoate and sorbic acid. Dispersing or wetting agents include but are not limited to poly(ethylene glycol), glycerol, bovine serum albumin, Tween®, Span®.

Compositions of the invention may also be formulated as a depot preparation, which may be administered by implantation or by intramuscular injection.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

The compounds of this invention can also be administered in sustained release forms or from sustained release drug delivery systems.

According to a particular embodiment, compositions according to the invention are for subcutaneous use.

In another particular aspect, the compositions according to the invention are adapted for delivery by repeated administration.

Further materials as well as formulation processing techniques and the like are set out in *Part 5 of Remington's "The Science and Practice of Pharmacy"*, 22$^{nd}$ Edition, 2012, *University of the Sciences in Philadelphia, Lippincott Williams & Wilkins*, which is incorporated herein by reference.

Another aspect of the invention is to provide a method of preparing a pharmaceutical composition according to the invention comprising the step of mixing a cell penetrating peptide or complex according to the invention or cells, in particular antigen-presenting cells, loaded with a complex according to the invention, and a pharmaceutically acceptable carrier.

The complex according to the invention, cells, in particular antigen-presenting cells, loaded with a complex according to the invention, compositions according to the invention, formulations thereof or a method according to the invention are useful in the prevention and/or treatment of a disease or a disorder, in particular those that can be treated or prevented by immunotherapy such as cancers and infectious diseases.

In another aspect, the invention provides imaging or diagnosis compositions. A still other aspect concerns methods for delivering an imaging agent and methods for diagnosing a disease or disorder in a subject, preferably a mammalian subject, and most preferably a human patient who is suspected of suffering from a medical disorder, and in particular a cancer, infectious disease, autoimmunity disorder and transplant rejection.

The formulations and modes of administration described herewith for the pharmaceutical compositions can also be suitable to the imaging or diagnosis compositions according to the invention.

In a further aspect, the present invention also relates to a kit-of-parts comprising at least one of:
(a) a cell penetrating peptide according to the invention;
(b) a complex according to the invention;
(c) a nucleic acid according to the invention;
(d) a vector according to the invention;
(e) a host cell according to the invention;
(f) a cell loaded with a complex according to the invention.

In a particular embodiment, the kit-of-parts of the invention comprises more than one component under (a) to (f).

In an illustration of the invention, the kit-of-parts comprises at least two different peptides under (a), at least two different complexes under (b), at least two different nucleic acids under (c), at least two different vectors under (d), at least two different host cells under (e), and/or at least two different cells under (f).

In another illustration, the kit-of-parts of the invention comprises at least two different complexes and/or at least two different nucleic acids according to the invention.

In particular, the kit-of-parts of the invention can comprise more than one complex according to the invention, for instance at least two complexes wherein each complex comprises one or more cargo molecules and wherein said cargo molecules are different between the complexes.

In an illustration, the kit-of-parts of the invention comprises at least 2 complexes, wherein each complex comprises one or more epitopes and wherein said epitopes are different between the complexes.

In another illustration, the kit-of-parts of the invention comprises at least 2 complexes, wherein each complex comprises one or more nucleic acids encoding one or more epitopes and wherein said nucleic acids are different between the complexes.

The various components of the kit-of-parts may be packaged in one or more containers. The above components may be provided in a lyophilized or dry form or dissolved in a suitable buffer. The kit may also comprise additional reagents including, for instance, preservatives, growth media, and/or buffers for storage and/or reconstitution of the above-referenced components, washing solutions, and the like. In another embodiment, the kit-of-parts according to the invention also contains instructions of use.

Another aspect of the invention is a vaccination kit for treating, preventing or stabilizing a cancer or an infectious disease, comprising the pharmaceutical composition according to the invention and instructions for use of said pharmaceutical composition.

In a particular embodiment, the compositions and/or the kit-of-parts according to the invention are for use in imaging techniques.

In another embodiment, the compositions and/or kit-of-parts according to the invention are for use in diagnosis of disease or disorder as mentioned along the present application.

Use and Methods According to the Invention

One aspect of the invention provides a method for delivering a cargo molecule into a cell in vitro, comprising the step of placing said cell into contact with a cell penetrating peptide according to the invention and said cargo molecule.

In a particular aspect, the method of the invention for delivering a cargo molecule into a cell in vitro comprises the steps of:

a) forming a complex between a cell penetrating peptide according to the invention and the cargo molecule to be delivered into a cell, and
b) placing said cell into contact with the complex formed in step a).

Another aspect of the invention provides an in vitro method for delivering and presenting the epitopes from a cargo molecule at the surface of a cell in an MHC class I and/or MHC class II context, comprising the step of placing said cell into contact with a cell penetrating peptide according to the invention and said cargo molecule.

In another aspect, the invention provides the use of any one of: (i) a complex of the invention, (ii) cells, such as antigen-presenting cells, loaded with a complex of the invention, for the preparation of a medicament for the prevention, treatment or stabilization of a disease or disorder, such as those which can be treated by immunotherapy, including cancers, infectious diseases, autoimmunity disorders and transplant rejections.

In an advantageous embodiment of the invention is provided a complex according to the invention comprising a cell penetrating peptide and epitopes, allowing the transport and presentation of said epitopes at the cell surface of antigen presenting cells in an MHC class I and/or MHC class II context, for use in vaccination and/or immunotherapy.

According to another aspect, the invention provides a method of preventing, treating or repressing a disease or disorder such as those which can be treated by immunotherapy, including cancers, infectious diseases, autoimmunity disorders and transplant rejections, wherein said method comprises administering any one of: (i) a complex of the invention, (ii) cells, such as antigen-presenting cells, loaded with a complex of the invention, or (iii) a pharmaceutical formulation of (i) to (ii), to said subject.

According to another embodiment, it is provided a method for eliciting or improving, in a subject, an immune response against one or multiple epitopes that is dependent on $CD4^+$ helper T cells and/or $CD8^+$ cytotoxic T cells, wherein said method comprises administering any one of: (i) a complex of the invention comprising a cargo molecule containing one or multiple epitope(s), (ii) cells, such as antigen-presenting cells, loaded with said complex, or (iii) a pharmaceutical formulation of (i) to (ii), to said subject.

An immune response that is dependent on $CD4^+$ and/or $CD8^+$ response can be determined by evaluating an inflammatory response, a pro-inflammatory cytokine response, including an increase in the expression of one or more of IFN-$\gamma$, TNF-$\alpha$ and IL-2 mRNA or protein relative to the level before administration of the compounds of the invention. It can also be measured by an increase in the frequency or absolute number of antigen-specific T cells after administration of the compounds of the invention, measured by HLA-peptide multimer staining, ELISPOT assays, and delayed type hypersensitivity tests. It can also be indirectly measured by an increase in antigen-specific serum antibodies that are dependent on antigen-specific T helper cells.

According to another embodiment, it is provided a method for eliciting or improving, in a subject, an immune response against one or multiple epitopes that is restricted by multiple MHC class I molecules and/or multiple MHC class II molecules, wherein said method comprises administering any one of: (i) a complex of the invention comprising a cargo molecule containing one or multiple epitope(s), (ii) cells, such as antigen-presenting cells, loaded with said complex, or (iii) a pharmaceutical formulation of (i) to (ii), to said subject.

A method for eliciting or improving, in a subject, an immune response against multiple epitopes that is restricted by multiple MHC class I molecules and/or multiple MHC class II molecules can be determined by evaluating a cytokine response, including an increase in the expression of one or more of IFN-γ, TNF-α and IL-2 mRNA or protein relative to the level before administration of the compounds of the invention, after in vitro stimulation of T cells with individual peptides binding to discrete MHC class I and class II molecules on antigen presenting cells. Restriction to different MHC molecules can also be validated by using antigen presenting cells expressing different MHC molecules, or by using MHC blocking antibodies. It can also be measured by an increase in the frequency or absolute number of antigen-specific T cells after administration of the compounds of the invention, measured by HLA-peptide multimer staining, which uses multimers assembled with discrete MHC molecules.

In a preferred aspect of the methods for eliciting or improving an immune response against one or multiple epitopes according to the invention, the immune response is directed against one or multiple epitopes of a tumor-associated antigen or a tumor-specific antigen as, for instance, a combination of glioma epitopes such as those described in Novellino et al. (2005, *Cancer Immunol Immunother*, 54(3): 187-207) and Vigneron et al. (2013, *Cancer Immun*.13:15).

In another preferred aspect, the immune response is directed against multiple epitopes of an antigenic protein from a pathogen.

In a particular aspect of the methods according to the invention, said methods are for eliciting or improving, in a subject, an immune response against one or multiple epitopes that is restricted by MHC class I molecules and/or MHC class II molecules.

In another aspect, the invention provides the use of any one of: (i) a complex of the invention, (ii) cells, such as antigen-presenting cells, loaded with the complex of the invention, for the preparation of an imaging composition for imaging techniques or for the preparation of a diagnosis composition for diagnosing a disease or disorder, respectively. The diseases or disorders that can be diagnosed with the invention include those which can be treated by immunotherapy, for instance cancers, infectious diseases, autoimmunity disorders and transplant rejections.

According to another aspect, the invention provides an imaging method wherein said method comprises using, in vitro, ex vivo or in vivo, any one of: (i) a complex of the invention, (ii) cells, such as antigen-presenting cells, loaded with the complex of the invention, or (iii) a pharmaceutical formulation of (i) to (ii).

According to a further aspect, the invention provides a method of diagnosing a disease or disorder in a subject, wherein said method comprises administering any one of: (i) a complex of the invention, (ii) cells, such as antigen-presenting cells, loaded with the complex of the invention, or (iii) a pharmaceutical formulation of (i) to (ii), to said subject or to said subject's sample ex vivo.

In a particular embodiment, uses and methods of the invention comprise administration of a complex according to the invention.

In another particular embodiment, uses and methods of the invention comprise administration of more than one complex, cells, or pharmaceutical formulation according to the invention.

In an illustration of the uses and methods of the invention, at least 2 complexes are used or administered, wherein each complex comprises one or more cargo molecules and said cargo molecules are different between the complexes.

In another illustration of the uses and methods of the invention, at least 2 complexes are used or administered, wherein each complex comprises one or more epitopes and wherein said epitopes are different between the complexes.

In a still further illustration of the uses and methods of the invention, at least 2 complexes are used or administered, wherein each complex comprises one or more nucleic acids encoding one or more epitopes and wherein said nucleic acids are different between the complexes.

Examples of cancers for the uses and methods of the invention include brain cancer, prostate cancer, breast cancer, ovarian cancer, esophageal cancer, lung cancer, liver cancer, kidney cancer, melanoma, gut carcinoma, lung carcinoma, head and neck squamous cell carcinoma, chronic myeloid leukemia, colorectal carcinoma, gastric carcinoma, endometrial carcinoma, myeloid leukemia, lung squamous cell carcinoma, acute lymphoblastic leukemia, acute myelogenous leukemia, bladder tumor, promyelocytic leukemia, non-small cell lung carcinoma, sarcoma.

The cancer may be a solid tumor, blood cancer, or lymphatic cancer. The cancer may be benign or metastatic.

Examples of infectious diseases for the uses and methods of the invention include diseases caused by viruses, bacteria, fungi, protozoa and multicellular parasites. They include, for instance, Amoebiasis, Anthrax, Buruli Ulcer (*Mycobacterium ulcerans*), Caliciviruses associated diarrhoea, Campylobacter diarrhoea, Cervical Cancer (Human papillomavirus), *Chlamydia trachomatis* associated genital diseases, Cholera, Crimean-Congo haemorrhagic fever, Dengue Fever, Diptheria, Ebola haemorrhagic fever, Enterotoxigenic *Escherichia coli* (ETEC) diarrhoea, Gastric Cancer (*Helicobacter pylori*), Gonorrhea, Group A Streptococcus associated diseases, Group B Streptococcus associated diseases, *Haemophilus influenzae* B pneumonia and invasive disease, Hepatitis A, Hepatitis B, Hepatitis C, Hepatitis E diarrhoea, Herpes simplex type 2 genital ulcers, HIV/AIDS, Hookworm Disease, Influenza, Japanese encephalitis, Lassa Fever, Leishmaniasis, Leptospirosi, Liver cancer (Hepatitis B), Liver Cancer (Hepatitis C), Lyme Disease, Malaria, Marburg haemorrhagic fever, Measles, Mumps, Nasopharyngeal cancer (Epstein-Barr virus), *Neisseria meningitidis* Meningitis, Parainfluenza associated pneumonia, Pertussis, Plague, Poliomyelitis, Rabies, Respiratory syncytial virus (RSV) pneumonia, Rift Valley fever, Rotavirus diarrhoea, Rubella, Schistosomiasis, Severe Acute Respiratory Syndrome (SARS), Shigellosis, Smallpox, *Staphylococcus aureus* associated diseases, Stomach Cancer (*Helicobacter pylori*), *Streptococcus pneumoniae* and invasive disease, Tetanus, Tick-borne encephalitis, Trachoma, Tuberculosis, Tularaemia, Typhoid fever, West-Nile virus associated disease, Yellow fever.

In another embodiment of the use and method of the invention, the cells according to the invention are antigen presenting cells, in particular dendritic cells, more particularly dendritic cells from the subject to be treated.

Typically, for cancer treatment, the therapeutically effective dose of a polypeptide according to the invention is from about 0.1 mg to 2 mg per injection or from about μmol to 1 mmol per injection.

Typically, for cancer treatment, the therapeutically effective dose of an antigen presenting cell loaded with a polypeptide according to the invention is from about 0.2 million cells to 2 million cells per injection.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Mode of Administration

Compounds, compositions, in particular vaccine compositions, and formulations thereof according to this invention may be administered in any manner including orally, parenterally, intravenously, rectally, or combinations thereof. Parenteral administration includes, but is not limited to, intravenous, intra-arterial, intra-peritoneal, subcutaneous, intradermal and intramuscular. The compositions of this invention may also be administered via topical, intratumoral, intranasal, or intranodal route. The compositions of this invention may also be administered in the form of an implant, which allows slow release of the compositions as well as a slow controlled i.v. infusion.

Preferentially, the compounds, compositions, in particular vaccine compositions, and formulations thereof according to the invention are administered subcutaneously.

In one embodiment of the invention, the administration of complex, antigen presenting cells and compositions of the invention requires multiple successive injections. Thus, the administration can be repeated at least two times, once as primary immunization injections and, later, as booster injections.

In a particular embodiment of the invention, the vaccine composition may be administered repeatedly or continuously. The vaccine composition can be administered repeatedly or continuously for a period of at least 1, 2, 3, or 4 weeks; 2, 3, 4, 5, 6, 8, 10, or 12 months; or 2, 3, 4, or 5 years.

In another embodiment, the cell penetrating peptide and the cargo molecule composing the complex according to the invention are contained in separate compositions which are mixed just before administration or which are administered simultaneously to the subject in need thereof.

Combination

According to a further embodiment, the administration of the pharmaceutical compositions in the methods and uses according to the invention can be carried out alone or in combination with a co-agent useful for treating and/or stabilizing the disease or disorder to be treated or repressed.

For instance, in the case of treatment, prevention, or stabilization of a cancer, the administration of the pharmaceutical compositions in the methods and uses according to the invention can be carried out in combination with substances used in conventional chemotherapy directed against solid tumors and for control of establishment of metastases or any other molecule that act by triggering programmed cell death e.g. for example a co-agent selected from Tumor Necrosis Family Members including, but not limited, to Fas Ligand and tumor necrosis factor (TNF)-related apoptosis inducing (TRAIL) ligand. According to a further embodiment, the administration of the pharmaceutical compositions in the methods and uses according to the invention can be carried out in parallel of radiotherapy.

The invention encompasses the administration of a complex of the invention, cell loaded with the complex of the invention, or a pharmaceutical composition thereof according to the invention, wherein it is administered to a subject prior to, simultaneously or sequentially with other therapeutic regimens or co-agents useful for treating, and/or stabilizing a cancer and/or preventing cancer relapsing (e.g. multiple drug regimens), in a therapeutically effective amount. Said complex, cell, or pharmaceutical composition, that is administered simultaneously with said co-agents can be administered in the same or different composition(s) and by the same or different route(s) of administration.

Said other therapeutic regimens or co-agents may be selected from the group consisting of radiation therapy, chemotherapy, surgery, targeted therapy (including small molecules, peptides and monoclonal antibodies), and anti-angiogenic therapy. Anti-angiogenic therapy is defined herein as the administration of an agent that directly or indirectly targets tumor-associated vasculature.

According to one embodiment, is provided a pharmaceutical formulation comprising a complex of the invention or a cell of the invention, in particular an antigen-presenting cell of the invention, combined with at least one co-agent useful for treating and/or stabilizing a cancer and/or preventing a cancer relapsing, and at least one pharmaceutically acceptable carrier.

According to another embodiment of the invention, the compounds according to the invention and pharmaceutical formulations thereof can be administered after surgery where solid tumors have been removed as a prophylaxis against relapsing and/or metastases.

According to a further embodiment, the administration of the imaging or diagnosis composition in the methods and uses according to the invention can be carried out alone or in combination with a co-agent useful for imaging and/or diagnosing the suspected disease or disorder.

Patients

Depending on the therapeutic effect of the cargo molecule, the invention can be applied to any patient susceptible to, or suffering from any disease or disorder that can be prevented, treated, or reduced by the action of said cargo molecule. When the cargo molecule comprises epitopes, the therapeutic effect of said cargo molecule may be to elicit an immune response directed against said epitopes, in particular a response that is dependent on $CD4^+$ helper T cells and/or $CD8^+$ cytotoxic T cells and/or that is restricted by MHC class I molecules and/or MHC class II molecules.

In one embodiment, patients according to the invention are patients susceptible to, or suffering from a cancer, for instance from a cancer of the brain, colon, head or neck, or from a cervical cancer.

In a particular embodiment, patients according to the invention are patients suffering from a brain cancer including glioma.

In a particular embodiment, patients according to the invention have been subjected to a surgical removal of a tumor.

In another embodiment, patients according to the invention are patients susceptible to, or suffering from an infectious disease.

References cited herein are hereby incorporated by reference in their entirety. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

The invention having been described, the following examples are presented by way of illustration, and not limitation.

EXAMPLES

The following examples have been conducted to support the effectiveness of some fragments of ZEBRA as cell penetrating peptides for delivery of peptides and proteins into the cell and the induction of an immune response in vivo.

The following abbreviations refer respectively to the definitions below:

aa (amino acid), h (hour), µl (microliter), µM (micromolar), mM (millimolar), mg (milligram), min (minute), CFSE (carboxyfluorescein succinimidyl ester), DC (dendritic cells).

Example 1

Preparation of the Fusion Polypeptides Comprising CPP1 or CPP2 of the Present Invention and an Ovalbumine Peptide Cargo Two CPPs and two fusion polypeptides corresponding to constructs 1 and 2, which comprised, respectively, one of two CPPs derived from ZEBRA and the immunodominant CD8$^+$ T cell epitope from ovalbumin, were chemically synthesized. The amino acid sequence of these CPPs and fusion polypeptides were as follows:

CPP1: (17 amino acids in total)

SEQ ID NO: 1:
KRYKNRVASRKSRAKFK

CPP2: (30 amino acids in total)

SEQ ID NO: 2:
KRYKNRVASRKSRAKFKQLLQHYREVAAAK

Ovalbumin CD8 epitope (8 amino acids in total)

SEQ ID NO: 3:
SIINFEKL

Complex 1: Construct 1: comprising CPP1 fused to Ovalbumin CD8 epitope (33 amino acids in total)

SEQ ID NO: 4:
KRYKNRVASRKSRAKFKEQLESIINFEKLTEWT

Complex 2: Construct 2: comprising CPP2 fused to Ovalbumin CD8 epitope (46 amino acids in total)

SEQ ID NO: 5:
KRYKNRVASRKSRAKFKQLLQHYREVAAAKEQLESIINFEKLTEWT

Example 2

Delivery and MHC Class I Restricted Presentation After Loading of CPP1-OVA or CPP2-OVA Fusion Polypeptides According to the Invention into Dendritic Cells The capacity of the CPP1 and CPP2 to be taken up by antigen presenting cells, with processing and presentation of the ovalbumin epitope, was first tested in vitro. Each of constructs 1 and 2 was added to cultures of bone-marrow derived dendritic cells, which were subsequently matured overnight with lipopolysaccharide (LPS). Processing and presentation of the ovalbumin epitope on MHC class I molecules was then detected in a functional assay, by co-culturing dendritic cells with ovalbumin-specific CD8$^+$ T cells derived from spleens of OT1 transgenic mice. The OT1 CD8$^+$ T cells were previously labelled with the fluorescent dye CFSE, which serves as an indicator of antigen-specific proliferation since it is diluted with each cell division. After 5 days of co-incubation of CD8$^+$ OT1 T cells and dendritic cells loaded with each of constructs 1 and 2, proliferation was assessed by flow cytometry (FIG. 1).

The polypeptides corresponding to constructs 1 and 2 were able to induce comparable proliferation of OT1 T cells (93-96% of T cells had proliferated, based on CFSE dilution). Moreover, viability of cells in the cultures was also similar (69-75%). This proliferation was similar and viability was superior to positive control cultures in which synthetic peptide corresponding to the minimal T cell epitope (SIINFEKL) was added (FIGS. 1C, 1D). Proliferation was also ovalbumin-specific, since few viable OT1 T cells were detected after culture alone or co-cultured with dendritic cells without antigen (FIGS. 1A, 1B).

Example 3

Figure 2:
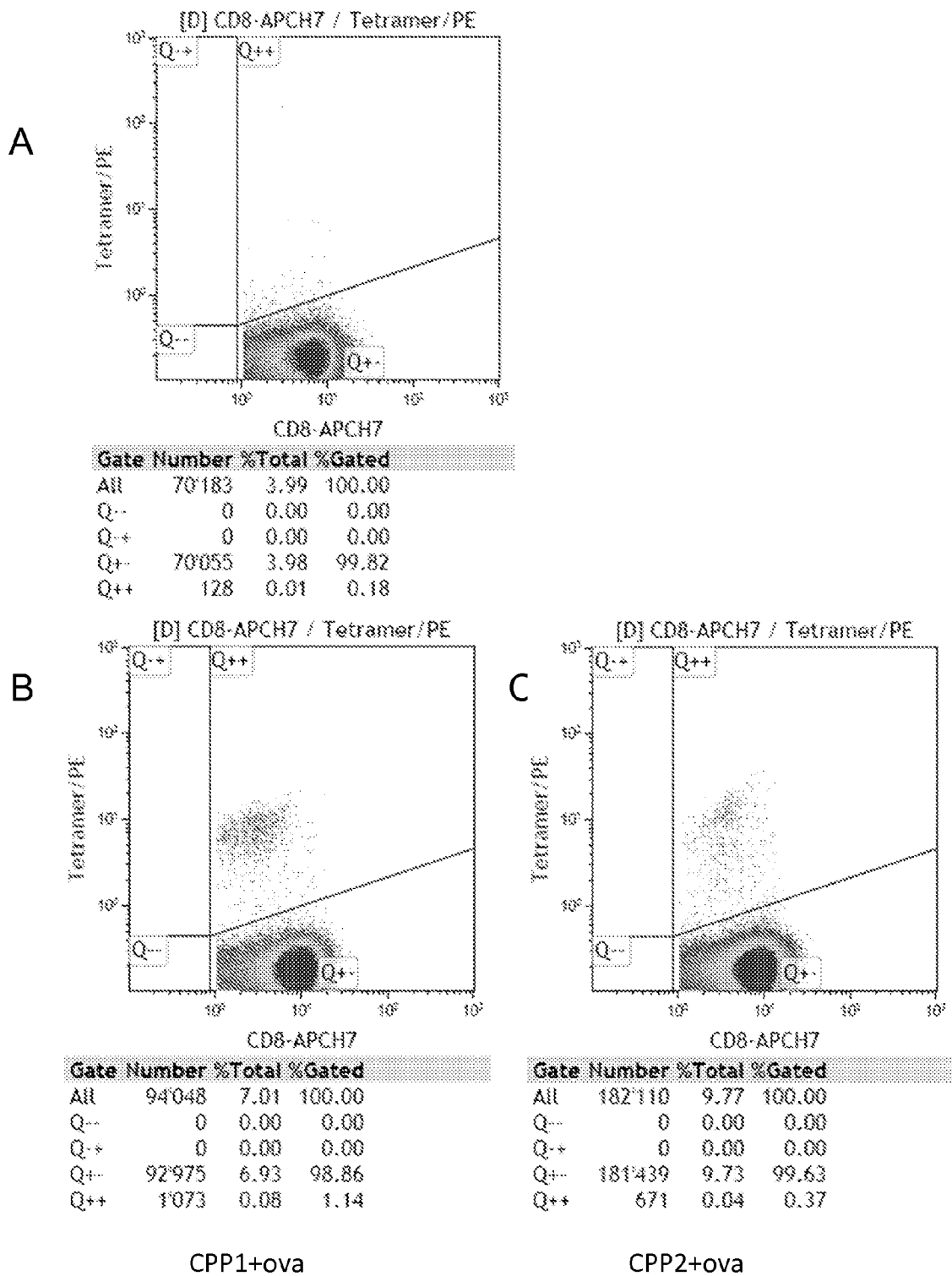
FIG. 2 shows polyclonal immune response after vaccination of mice with the fusion polypeptides comprising CPP1 or CPP2 and an ovalbumine peptide cargo. Mice were vaccinated twice sub-cutaneously at 14 days of interval with 20 µg of each CPPs-OVA fusion polypeptides and 100 µg anti-CD40, 50 µg poly-IC was injected intramuscularly 10 days after the boost, the mice were sacrificed and the splenocytes stained with a multimer and anti-CD8. Negative control with PBS (A); CPP1-OVA (B); CPP2-OVA (C).

Vaccination of Mice with CPP1-OVA or CPP2-OVA Fusion Polypeptides of the Present Invention To test the capacity of the polypeptides corresponding to constructs 1 and 2 to stimulate antigen-specific CD8$^+$ T cells in more stringent conditions, they were tested in vivo in a vaccination protocol (FIG. 2). In order to elicit an in vivo response, the polypeptide vaccine must be taken up by naturally present antigen presenting cells in the injected animal, and stimulation of polyclonal T cells must be highly efficient if ovalbumin-specific T cells are to be detected ex vivo. The read-out for these experiments was flow cytometry of splenocytes, using MHC-peptide multimers to detect ovalbumin-specific CD8$^+$ T cells.

After only 2 vaccinations, an elevated proportion of ovalbumin-specific CD8$^+$ T cells was detected for the two vaccination groups (0.37-1.14% of CD8$^+$ T cells were multimer positive, compared with 0.18% for mice vaccinated with PBS (negative control). The peptide corresponding to construct 2 was particularly efficacious in vivo since it elicited over 1% ovalbumin-specific CD8$^+$ T cells.

Conclusion: Overall these data confirm the functionality of CPPs 1 and 2 as cell penetrating peptides. They also confirm that the polypeptides corresponding to constructs 1 and constructs 2, which comprise each of these two CPPs, respectively, and an ovalbumin T cell epitope, can be taken up by dendritic cells, and that the cargo molecule (i.e. the T cell epitope contained in the construction) is cross-presented to CD8$^+$ T cells in vitro and in the context of in vivo vaccination.

Example 4

In Vitro Transduction Experiment with Different CPP-OVA Fusion Polypeptides of the Invention Transduction into cells was monitored using different CPP-OVA fusion polypeptides comprising CPP1, CPP2, CPP8, or CPP10. Each of these CPPs fused with the immunodominant CD8$^+$ T cell epitope from ovalbumin were chemically synthesized and labeled with fluorescein. $5.10^5$ cells were incubated for 2 h at 37° C. with 0.9 µM of the different fusion polypeptides. The cells tested were human lymphoid cells K562, murine lymphoid cells EL4, human astrocytoma cells U251 and murine astrocytoma cells GL261. The cells were washed in an acid buffer to remove all the membrane bound peptide and stained for viability with Live-Dead Yellow. Analysis was performed by flow cytometry. The index of fluorescence indicates the level of fluorescence above the natural auto-fluorescence of the cells. It is the ratio of the mean fluorescence index measured by flow cytometry between the cells alone and the cells loaded with CPP-OVA fusion polypeptides.

The results are presented in Table 2.

TABLE 2

|  | K562 | EL4 | U251 | GL261 |
|---|---|---|---|---|
| CPP1 (SEQ ID NO: 1) | 3 | 4.8 | 4.5 | 2.4 |
| CPP2 (SEQ ID NO: 2) | 15 | 57.7 | 25.1 | 20.8 |
| CPP8 (SEQ ID NO: 8) | 1.9 | 2.5 | 2 | 1.4 |
| CPP10 (SEQ ID NO: 9) | 3.7 | 4 | 4 | 1.9 |

Overall, no toxic effect of the CPP-OVA fusion polypeptides was observed. Furthermore, these results demonstrate that all the tested CPPs can penetrate the cells of human or murine origin with similar efficiency.

Example 5

In Vivo Vaccination of Mice with Different CPP-OVA Fusion Polypeptides of the Invention The experiment was performed as described in Example 3.

Four to eight mice per group were vaccinated twice subcutaneously at 14 days of interval with 10 nmol of fusion polypeptides comprising one of the CPPs indicated in Table 2 fused to the ovalbumin CD8+ epitope (SEQ ID NO: 3) flanked by the spacers of SEQ ID NO: 11 and SEQ ID NO: 12 at the N-terminal and C-terminal part of the CD8+ epitope, respectively. Each CPP-OVA fusion polypeptide was injected in PBS with 100 µg anti-CD40. 50 µg poly-IC was injected intramuscularly 7 days after the second vaccination. Immune response was monitored in the blood with a Pentamer staining followed by flow cytometry analysis.

The results are presented in Table 3 as fold increase relative to a CPP-OVA fusion polypeptide of reference comprising CPP14 of SEQ ID NO: 22. As can be seen from Table 2, all CPP-OVA fusion polypeptides tested had a higher immunogenic potential compared to the reference fusion polypeptide comprising CPP14 except for another reference fusion polypeptide comprising CPP7 of SEQ ID NO: 21 that constitutes a negative control and that had a lower immunogenic potential compared to the reference fusion polypeptide comprising CPP14.

TABLE 3

| CPP-OVA fusion polypeptide, wherein CPP is | Fold increase in proliferation compared to CPP14 |
|---|---|
| CPP7 (SEQ ID NO: 21) | 0.65 |
| CPP1 (SEQ ID NO: 1) | 1.74 |
| CPP2 (SEQ ID NO: 2) | 1.41 |
| CPP8 (SEQ ID NO: 8) | 1.28 |
| CP10 (SEQ ID NO: 9) | 2.17 |

CPP7 is a 8-amino acid-long fragment of Zebra extending from positions 178 to 185 of Zebra.
CPP14 is a 42-amino acid-long fragment of Zebra extending from positions 178 to 219 of Zebra.

Conclusion: Taken together, results of Examples 4 and 5 show that the different CPPs of the invention can penetrate cells of human or murine origin and that the cargo molecule carried by such CPPs is cross-presented to CD8+ T cells, i.e. induce an immune response specific for the transported cargo molecule and, thus, find utility in vaccination and immunotherapy.

SEQUENCE LISTING

CPP1: (17 amino acids in total)

SEQ ID NO: 1:
KRYKNRVASRKSRAKFK

CPP2: (30 amino acids in total)

SEQ ID NO: 2:
KRYKNRVASRKSRAKFKQLLQHYREVAAAK

Ovalbumin CD8 epitope (8 amino acids in total)

SEQ ID NO: 3:
SIINFEKL

CPPs-OVA fusion polypeptides:
Construct 1: comprising CPP1 fused to Ovalbumin CD8 epitope (33 amino acids in total)

SEQ ID NO: 4:
KRYKNRVASRKSRAKFKEQLESIINFEKLTEWT

Construct 2: comprising CPP2 fused to Ovalbumin CD8 epitope (46 amino acids in total)

SEQ ID NO: 5:
KRYKNRVASRKSRAKFKQLLQHYREVAAAKEQLESIINFEKLTEWT

Artificial sequence

SEQ ID NO: 6:
$X_1X_2X_3X_4X_5X_6X_7X_8X_9X_{10}X_{11}SX_{13}X_{14}X_{15}X_{16}X_{17}$ $X_1$ is K, R, or H
$X_2$ is R, K, or H
$X_3$ is Y, W, or F
$X_4$ is K, R, or H
$X_5$ is N or Q
$X_6$ is R, K, or H
$X_7$ is V, I, M, L, F, or A
$X_8$ is A, V, L, I, or G
$X_9$ is S or T
$X_{10}$ is R, K, or H
$X_{11}$ is K, R, or H
$X_{13}$ is R, K, or H
$X_{14}$ is A, V, L, I, or G
$X_{15}$ is K, R, or H
$X_{16}$ is F, L, V, I, Y, W, or M
$X_{17}$ is K, R, or H
Artificial sequence SEQ ID NO: 7:
$X_1X_2X_3X_4X_5X_6X_7X_8X_9X_{10}X_{11}SX_{13}X_{14}X_{15}X_{16}X_{17}$ $X_1$ is K or R
$X_2$ is R or K
$X_3$ is Y, W, or F
$X_4$ is K or R X$_5$ is N or Q
X$_6$ is R or K
X$_7$ is V, I, M or L
X$_8$ is A or G
X$_9$ is S or T
X$_{10}$ is R or K
X$_{11}$ is K or R
X$_{13}$ is R or K
X$_{14}$ is A or G
X$_{15}$ is K or R
X$_{16}$ is F, Y, or W
X$_{17}$ is K or R CPP8: (15 amino acids in total)

SEQ ID NO: 8:
QHYREVAAAKSSEND

CPP10: (19 amino acids in total)

SEQ ID NO: 9:
REVAAAKSSENDRLRLLLK

CPP11: (25 amino acids in total)

SEQ ID NO: 10:
QLLQHYREVAAAKSSENDRLRLLLK

Spacers (Artificial sequences)

SEQ ID NO: 11:
EQLE

SEQ ID NO: 12:
TEWT

Artificial sequence (21 amino acids in total)

SEQ ID NO: 13:
LEIKRYKNRVASRKCRAKFKQ

Artificial sequence (21 amino acids in total)

SEQ ID NO: 14:
SELEIKRYKNRVASRKCRAKF

Enterokinase target site

SEQ ID NO: 15:
DDDK

Factor Xa target site

SEQ ID NO: 16:
IEDGR

Thrombin target site

SEQ ID NO: 17:
LVPRGS

Protease TEV target site

SEQ ID NO: 18:
ENLYFQG

PreScission protease target site

SEQ ID NO: 19:
LEVLFQGP

Furin target site

SEQ ID NO: 20:
RX$_2$X$_3$R

X$_2$ is any amino acid
X$_3$ is R or K

CPP7 (8 amino acids in total)

SEQ ID NO: 21:
KRYKNRVA

CPP14 (42 amino acids in total)

SEQ ID NO: 22:
KRYKNRVASRKCRAKFKQLLQHYREVAAAKSSENDRLRLLLK

ZEBRA amino acid sequence (natural sequence from Epstein-Barr virus (EBV)) (YP_401673)

SEQ ID NO: 23:
MMDPNSTSEDVKFTPDPYQVPFVQAFDQATRVYQDLGGPSQAPLPCVLWP

VLPEPLPQGQLTAYHVSTAPTGSWFSAPQPAPENAYQAYAAPQLFPVSDI

TQNQQTNQAGGEAPQPGDNSTVQTAAAVVFACPGANQGQQLADIGVPQPA

PVAAPARRTRKPQQPESLEECDSELEIKRYKNRVASRKCRAKFKQLLQHY

REVAAAKSSENDRLRLLLKQMCPSLDVDSIIPRTPDVLHEDLLNF

---

The invention claimed is:

1. A cell penetrating peptide consisting of a 15-30 amino acid fragment of the domain extending from residue 170 to residue 220 of SEQ ID NO: 23,
wherein, 1, 2, 3, 4, or 5 amino acids have been substituted, deleted, and/or added without aborting said peptide's cell penetrating ability, and
wherein said peptide has a Ser (S) at the equivalent of SEQ ID NO: 23 position 189.

2. The cell penetrating peptide according to claim 1, wherein said peptide has an amino acid sequence comprising:
(i) SEQ ID NO: 1 with 1, 2, 3, or 4 amino acids which are substituted, deleted and/or added without aborting said peptide's cell penetrating ability, or
(ii) SEQ ID NO: 6 with 1, 2, 3, or 4 amino acids which are substituted, deleted and/or added without aborting said peptide's cell penetrating ability, wherein
$X_1$ is K, R, or H
$X_2$ is R, K, or H
$X_3$ is Y, W, or F
$X_4$ is K, R, or H
$X_5$ is N or Q
$X_6$ is R, K, or H
$X_7$ is V, I, M, L, F, or A
$X_8$ is A, V, L, I, or G
$X_9$ is S or T
$X_{10}$ is R, K, or H
$X_{11}$ is K, R, or H
$X_{13}$ is R, K, or H
$X_{14}$ is A, V, L, I, or G
$X_{15}$ is K, R, or H
$X_{16}$ is F, L, V, I, Y, W, or M
$X_{17}$ is K, R, or H.

3. The cell penetrating peptide according to claim 1, wherein said peptide has an amino acid sequence comprising SEQ ID NO: 1 or SEQ ID NO: 2.

4. A complex comprising:
(1) a cell penetrating peptide consisting of a 15-30 amino acid fragment of the domain extending from residue 170 to residue 220 of SEQ ID NO: 23,
wherein, 1, 2, 3, 4, or 5 amino acids have been substituted, deleted, and/or added without aborting said peptide's cell penetrating ability,
and wherein the peptide includes a Ser (S) at the equivalent of SEQ ID NO: 23 position 189;
and
(2) a cargo molecule selected from the group consisting of: (i) a peptide, a polypeptide, or a protein, (ii) a polysaccharide, (iii) a lipid, (iv) a lipoprotein, (v) a glycolipid, and (vi) a nucleic acid, wherein the cargo molecule according to (i) comprises pathogen epitope(s) and/or tumor epitope(s).

5. The complex according to claim 4, wherein said cell penetrating peptide facilitates presentation of the epitope(s) of said cargo molecule at the cell surface in MHC class I and/or MHC class II context.

6. A nucleic acid encoding:
(1) a cell penetrating peptide consisting of a 15-30 amino acid fragment of the domain extending from residue 170 to residue 220 of SEQ ID NO: 23,
wherein, 1, 2, 3, 4, or 5 amino acids have been substituted, deleted, and/or added without aborting said peptide's cell penetrating ability, and
wherein said peptide has a Ser (S) at the equivalent of SEQ ID NO: 23 position 189; or
(2) an amino acid complex comprising said cell penetrating peptide covalently linked to a peptide, polypeptide or protein cargo molecule comprising pathogen epitope(s) and/or tumor epitope(s).

7. A vector comprising the nucleic acid according to claim 6.

8. A host cell comprising the vector according to claim 7.

9. A method of preparing the cell penetrating peptide according to claim 1, comprising cultivating a host cell comprising a vector comprising a nucleic acid encoding said cell penetrating peptide in a culture medium and separating said peptide from the culture medium or from the host cell lysate after host cell lysis.

10. An isolated cell loaded with a complex according to claim 4.

11. A cell according to claim 10, wherein said cell is an antigen presenting cell.

12. A composition comprising at least one of:
(a) a cell penetrating peptide consisting of a 15-30 amino acid fragment of the domain extending from residue 170 to residue 220 of SEQ ID NO: 23,
wherein, 1, 2, 3, 4, or 5 amino acids have been substituted, deleted, and/or added without aborting said peptide's cell penetrating ability,
wherein said peptide has a Ser (S) at the equivalent of SEQ ID NO: 23 position 189;
(b) a complex comprising:
(1) a cell penetrating peptide consisting of a 15-30 amino acid fragment of the domain extending from residue 170 to residue 220 of SEQ ID NO: 23,
wherein, 1, 2, 3, 4, or 5 amino acids have been substituted, deleted, and/or added without aborting said peptide's cell penetrating ability,
and wherein the peptide includes a Ser (S) at the equivalent of SEQ ID NO: 23 position 189; and
(2) a cargo molecule selected from the group consisting of: (i) a peptide, a polypeptide, or a protein, (ii) a polysaccharide, (iii) a lipid, (iv) a lipoprotein, (v) a glycolipid, and (vi) a nucleic acid, wherein the cargo molecule according to (i) is selected among pathogen epitopes and/or tumor epitopes;
(c) a nucleic acid encoding the cell penetrating peptide of (a) or encoding the complex of (b) wherein the cargo molecule of (b)(2) is a peptide, polypeptide or protein cargo molecule comprising pathogen epitope(s) and/or tumor epitope(s) covalently linked to the cell penetrating peptide of (b)(1);
(d) a vector comprising the nucleic acid of (c);
(e) an isolated host cell comprising the vector of (d);
(f) an isolated cell loaded with the complex of (b).

13. A pharmaceutical composition comprising:
(a) at least one cell penetrating peptide according to claim 1, and
(b) a pharmaceutically acceptable carrier.

14. A pharmaceutical composition comprising:
(a) at least one complex according to claim 4, and
(b) a pharmaceutically acceptable carrier.

15. The pharmaceutical composition according to claim 14, wherein said composition comprises at least two different complexes.

16. A method of preventing and/or treating a disease or disorder selected from the group consisting of cancers, infectious diseases, autoimmunity disorders and transplant rejections, comprising administering a complex according to claim 4 to a subject in need thereof.

17. A method of preventing and/or treating a disease or disorder selected from the group consisting of cancers, infectious diseases, autoimmunity disorders and transplant rejections, comprising administering a cell according to claim 10 to a subject in need thereof.

18. A method for delivering a cargo molecule into a cell in vitro, comprising the steps of:
a) forming a complex between a cell penetrating peptide according to claim 1 and the cargo molecule to be delivered into a cell, and
b) placing said cell into contact with the complex formed in step a).

19. The method according to claim 9, wherein the separated cell penetrating peptide is covalently linked to a peptide, polypeptide, or protein cargo molecule comprising pathogen epitope(s) and/or tumor epitope(s).

20. A pharmaceutical composition comprising:
(a) at least one host cell according to claim 8, and
(b) a pharmaceutically acceptable carrier.

21. A pharmaceutical composition comprising:
(a) at least one host cell comprising the complex according to claim 4, and
(b) a pharmaceutically acceptable carrier.

* * * * *

SEQUENCE LISTING

<160> NUMBER OF SEQ ID NOS: 23

<210> SEQ ID NO 1
<211> LENGTH: 17
<212> TYPE: PRT
<213> ORGANISM: Artificial Sequence
<220> FEATURE:
<223> OTHER INFORMATION: CCP1

<400> SEQUENCE: 1

Lys Arg Tyr Lys Asn Arg Val Ala Ser Arg Lys Ser Arg Ala Lys Phe
1               5                   10                  15

Lys

<210> SEQ ID NO 2
<211> LENGTH: 30
<212> TYPE: PRT
<213> ORGANISM: Artificial Sequence
<220> FEATURE:
<223> OTHER INFORMATION: CPP2

<400> SEQUENCE: 2

Lys Arg Tyr Lys Asn Arg Val Ala Ser Arg Lys Ser Arg Ala Lys Phe
1               5                   10                  15
Lys Gln Leu Leu Gln His Tyr Arg Glu Val Ala Ala Ala Lys
            20                  25                  30

<210> SEQ ID NO 3
<211> LENGTH: 8
<212> TYPE: PRT
<213> ORGANISM: Artificial Sequence
<220> FEATURE:
<223> OTHER INFORMATION: ovalbumine CD8 epitope

<400> SEQUENCE: 3

Ser Ile Ile Asn Phe Glu Lys Leu
1               5

<210> SEQ ID NO 4
<211> LENGTH: 33
<212> TYPE: PRT
<213> ORGANISM: Artificial Sequence
<220> FEATURE:
<223> OTHER INFORMATION: CPP1-OVA fusion polypeptide

<400> SEQUENCE: 4

Lys Arg Tyr Lys Asn Arg Val Ala Ser Arg Lys Ser Arg Ala Lys Phe
1               5                   10                  15
Lys Glu Gln Leu Glu Ser Ile Ile Asn Phe Glu Lys Leu Thr Glu Trp
            20                  25                  30
Thr

<210> SEQ ID NO 5
<211> LENGTH: 46
<212> TYPE: PRT
<213> ORGANISM: Artificial Sequence
<220> FEATURE:
<223> OTHER INFORMATION: CPP2-OVA fusion polypeptide

<400> SEQUENCE: 5

Lys Arg Tyr Lys Asn Arg Val Ala Ser Arg Lys Ser Arg Ala Lys Phe
1               5                   10                  15
Lys Gln Leu Leu Gln His Tyr Arg Glu Val Ala Ala Ala Lys Glu Gln
            20                  25                  30
Leu Glu Ser Ile Ile Asn Phe Glu Lys Leu Thr Glu Trp Thr
                35                  40                  45

<210> SEQ ID NO 6
<211> LENGTH: 17
<212> TYPE: PRT
<213> ORGANISM: Artificial Sequence
<220> FEATURE:
<223> OTHER INFORMATION: Generic sequence
<220> FEATURE:
<221> NAME/KEY: MISC_FEATURE
<222> LOCATION: (1)..(1)

<223> OTHER INFORMATION: Xaa is K, R, or H
<220> FEATURE:
<221> NAME/KEY: MISC_FEATURE
<222> LOCATION: (2)..(2)
<223> OTHER INFORMATION: Xaa is R, K, or H
<220> FEATURE:
<221> NAME/KEY: MISC_FEATURE
<222> LOCATION: (3)..(3)
<223> OTHER INFORMATION: Xaa is Y, W, or F
<220> FEATURE:
<221> NAME/KEY: MISC_FEATURE
<222> LOCATION: (4)..(4)
<223> OTHER INFORMATION: Xaa is K, R, or H
<220> FEATURE:
<221> NAME/KEY: MISC_FEATURE
<222> LOCATION: (5)..(5)
<223> OTHER INFORMATION: Xaa is N or Q
<220> FEATURE:
<221> NAME/KEY: MISC_FEATURE
<222> LOCATION: (6)..(6)
<223> OTHER INFORMATION: Xaa is R, K, or H
<220> FEATURE:
<221> NAME/KEY: MISC_FEATURE
<222> LOCATION: (7)..(7)
<223> OTHER INFORMATION: Xaa is V, I, M, L, F, or A
<220> FEATURE:
<221> NAME/KEY: MISC_FEATURE
<222> LOCATION: (8)..(8)
<223> OTHER INFORMATION: Xaa is A, V, L, I, or G
<220> FEATURE:
<221> NAME/KEY: MISC_FEATURE
<222> LOCATION: (9)..(9)
<223> OTHER INFORMATION: Xaa is S or T
<220> FEATURE:
<221> NAME/KEY: MISC_FEATURE
<222> LOCATION: (10)..(10)
<223> OTHER INFORMATION: Xaa is R, K, or H
<220> FEATURE:
<221> NAME/KEY: MISC_FEATURE
<222> LOCATION: (11)..(11)
<223> OTHER INFORMATION: Xaa is K, R, or H
<220> FEATURE:
<221> NAME/KEY: MISC_FEATURE
<222> LOCATION: (13)..(13)
<223> OTHER INFORMATION: Xaa is R, K, or H
<220> FEATURE:
<221> NAME/KEY: MISC_FEATURE
<222> LOCATION: (14)..(14)
<223> OTHER INFORMATION: Xaa is A, V, L, I, or G
<220> FEATURE:
<221> NAME/KEY: MISC_FEATURE
<222> LOCATION: (15)..(15)
<223> OTHER INFORMATION: Xaa is K, R, or H
<220> FEATURE:
<221> NAME/KEY: MISC_FEATURE
<222> LOCATION: (16)..(16)
<223> OTHER INFORMATION: Xaa is F, L, V, I, Y, W, or M
<220> FEATURE:
<221> NAME/KEY: MISC_FEATURE
<222> LOCATION: (17)..(17)
<223> OTHER INFORMATION: Xaa is K, R, or H

<400> SEQUENCE: 6

Xaa Xaa Xaa Xaa Xaa Xaa Xaa Xaa Xaa Xaa Xaa Ser Xaa Xaa Xaa Xaa
1               5                   10                  15

Xaa

<210> SEQ ID NO 7
<211> LENGTH: 17
<212> TYPE: PRT
<213> ORGANISM: artificial sequence
<220> FEATURE:
<223> OTHER INFORMATION: Generic sequence
<220> FEATURE:
<221> NAME/KEY: MISC_FEATURE
<222> LOCATION: (1)..(1)

```
<223> OTHER INFORMATION: Xaa is K or R
<220> FEATURE:
<221> NAME/KEY: MISC_FEATURE
<222> LOCATION: (2)..(2)
<223> OTHER INFORMATION: Xaa is R or K
<220> FEATURE:
<221> NAME/KEY: MISC_FEATURE
<222> LOCATION: (3)..(3)
<223> OTHER INFORMATION: Xaa is Y, W, or F
<220> FEATURE:
<221> NAME/KEY: MISC_FEATURE
<222> LOCATION: (4)..(4)
<223> OTHER INFORMATION: Xaa is K or R
<220> FEATURE:
<221> NAME/KEY: MISC_FEATURE
<222> LOCATION: (5)..(5)
<223> OTHER INFORMATION: Xaa is N or Q
<220> FEATURE:
<221> NAME/KEY: MISC_FEATURE
<222> LOCATION: (6)..(6)
<223> OTHER INFORMATION: Xaa is R or K
<220> FEATURE:
<221> NAME/KEY: MISC_FEATURE
<222> LOCATION: (7)..(7)
<223> OTHER INFORMATION: Xaa is V, I, M or L
<220> FEATURE:
<221> NAME/KEY: MISC_FEATURE
<222> LOCATION: (8)..(8)
<223> OTHER INFORMATION: Xaa is A or G
<220> FEATURE:
<221> NAME/KEY: MISC_FEATURE
<222> LOCATION: (9)..(9)
<223> OTHER INFORMATION: Xaa is S or T
<220> FEATURE:
<221> NAME/KEY: MISC_FEATURE
<222> LOCATION: (10)..(10)
<223> OTHER INFORMATION: Xaa is R or K
<220> FEATURE:
<221> NAME/KEY: MISC_FEATURE
<222> LOCATION: (11)..(11)
<223> OTHER INFORMATION: Xaa is K or R
<220> FEATURE:
<221> NAME/KEY: MISC_FEATURE
<222> LOCATION: (13)..(13)
<223> OTHER INFORMATION: Xaa is R or K
<220> FEATURE:
<221> NAME/KEY: MISC_FEATURE
<222> LOCATION: (14)..(14)
<223> OTHER INFORMATION: Xaa is A or G
<220> FEATURE:
<221> NAME/KEY: MISC_FEATURE
<222> LOCATION: (15)..(15)
<223> OTHER INFORMATION: Xaa is K or R
<220> FEATURE:
<221> NAME/KEY: MISC_FEATURE
<222> LOCATION: (16)..(16)
<223> OTHER INFORMATION: Xaa is F, Y, or W
<220> FEATURE:
<221> NAME/KEY: MISC_FEATURE
<222> LOCATION: (17)..(17)
<223> OTHER INFORMATION: Xaa is K or R

<400> SEQUENCE: 7

Xaa Xaa Xaa Xaa Xaa Xaa Xaa Xaa Xaa Xaa Xaa Ser Xaa Xaa Xaa Xaa
1               5                   10                  15

Xaa

<210> SEQ ID NO 8
<211> LENGTH: 15
<212> TYPE: PRT
<213> ORGANISM: artificial sequence
<220> FEATURE:
<223> OTHER INFORMATION: CPP8

<400> SEQUENCE: 8
```

Gln His Tyr Arg Glu Val Ala Ala Ala Lys Ser Ser Glu Asn Asp
1               5                   10                  15

<210> SEQ ID NO 9
<211> LENGTH: 19
<212> TYPE: PRT
<213> ORGANISM: artificial sequence
<220> FEATURE:
<223> OTHER INFORMATION: CPP10

<400> SEQUENCE: 9

Arg Glu Val Ala Ala Ala Lys Ser Ser Glu Asn Asp Arg Leu Arg Leu
1               5                   10                  15

Leu Leu Lys

<210> SEQ ID NO 10
<211> LENGTH: 25
<212> TYPE: PRT
<213> ORGANISM: artificial sequence
<220> FEATURE:
<223> OTHER INFORMATION: CPP11

<400> SEQUENCE: 10

Gln Leu Leu Gln His Tyr Arg Glu Val Ala Ala Ala Lys Ser Ser Glu
1               5                   10                  15

Asn Asp Arg Leu Arg Leu Leu Leu Lys
            20                  25

<210> SEQ ID NO 11
<211> LENGTH: 4
<212> TYPE: PRT
<213> ORGANISM: artificial sequence
<220> FEATURE:
<223> OTHER INFORMATION: spacer

<400> SEQUENCE: 11

Glu Gln Leu Glu
1

<210> SEQ ID NO 12
<211> LENGTH: 4
<212> TYPE: PRT
<213> ORGANISM: artificial sequence
<220> FEATURE:
<223> OTHER INFORMATION: spacer

<400> SEQUENCE: 12

Thr Glu Trp Thr
1

<210> SEQ ID NO 13
<211> LENGTH: 21
<212> TYPE: PRT
<213> ORGANISM: Artificial Sequence
<220> FEATURE:
<223> OTHER INFORMATION: fragment of Zebra

<400> SEQUENCE: 13

Leu Glu Ile Lys Arg Tyr Lys Asn Arg Val Ala Ser Arg Lys Cys Arg
1               5                   10                  15

Ala Lys Phe Lys Gln
            20

<210> SEQ ID NO 14
<211> LENGTH: 21

```
<212> TYPE: PRT
<213> ORGANISM: Artificial Sequence
<220> FEATURE:
<223> OTHER INFORMATION: fragment of Zebra

<400> SEQUENCE: 14

Ser Glu Leu Glu Ile Lys Arg Tyr Lys Asn Arg Val Ala Ser Arg Lys
1               5                   10                  15

Cys Arg Ala Lys Phe
            20

<210> SEQ ID NO 15
<211> LENGTH: 4
<212> TYPE: PRT
<213> ORGANISM: Artificial Sequence
<220> FEATURE:
<223> OTHER INFORMATION: Enterokinase target site

<400> SEQUENCE: 15

Asp Asp Asp Lys
1

<210> SEQ ID NO 16
<211> LENGTH: 5
<212> TYPE: PRT
<213> ORGANISM: Artificial Sequence
<220> FEATURE:
<223> OTHER INFORMATION: Factor Xa target site

<400> SEQUENCE: 16

Ile Glu Asp Gly Arg
1               5

<210> SEQ ID NO 17
<211> LENGTH: 6
<212> TYPE: PRT
<213> ORGANISM: Artificial Sequence
<220> FEATURE:
<223> OTHER INFORMATION: Thrombin target site

<400> SEQUENCE: 17

Leu Val Pro Arg Gly Ser
1               5

<210> SEQ ID NO 18
<211> LENGTH: 7
<212> TYPE: PRT
<213> ORGANISM: Artificial Sequence
<220> FEATURE:
<223> OTHER INFORMATION: Protease TEV target site

<400> SEQUENCE: 18

Glu Asn Leu Tyr Phe Gln Gly
1               5

<210> SEQ ID NO 19
<211> LENGTH: 8
<212> TYPE: PRT
<213> ORGANISM: Artificial Sequence
<220> FEATURE:
<223> OTHER INFORMATION: PreScission protease target site

<400> SEQUENCE: 19

Leu Glu Val Leu Phe Gln Gly Pro
1               5
```

<210> SEQ ID NO 20
<211> LENGTH: 4
<212> TYPE: PRT
<213> ORGANISM: Artificial Sequence
<220> FEATURE:
<223> OTHER INFORMATION: Furin target site
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is R or K

<400> SEQUENCE: 20

Arg Xaa Xaa Arg
1

<210> SEQ ID NO 21
<211> LENGTH: 8
<212> TYPE: PRT
<213> ORGANISM: Artificial Sequence
<220> FEATURE:
<223> OTHER INFORMATION: CPP6

<400> SEQUENCE: 21

Lys Arg Tyr Lys Asn Arg Val Ala
1               5

<210> SEQ ID NO 22
<211> LENGTH: 42
<212> TYPE: PRT
<213> ORGANISM: Artificial Sequence
<220> FEATURE:
<223> OTHER INFORMATION: CPP14

<400> SEQUENCE: 22

Lys Arg Tyr Lys Asn Arg Val Ala Ser Arg Lys Cys Arg Ala Lys Phe
1               5                   10                  15

Lys Gln Leu Leu Gln His Tyr Arg Glu Val Ala Ala Ala Lys Ser Ser
            20                  25                  30

Glu Asn Asp Arg Leu Arg Leu Leu Leu Lys
        35                  40

<210> SEQ ID NO 23
<211> LENGTH: 245
<212> TYPE: PRT
<213> ORGANISM: Epstein-Barr virus

<400> SEQUENCE: 23

Met Met Asp Pro Asn Ser Thr Ser Glu Asp Val Lys Phe Thr Pro Asp
1               5                   10                  15

Pro Tyr Gln Val Pro Phe Val Gln Ala Phe Asp Gln Ala Thr Arg Val
            20                  25                  30

Tyr Gln Asp Leu Gly Gly Pro Ser Gln Ala Pro Leu Pro Cys Val Leu
        35                  40                  45

Trp Pro Val Leu Pro Glu Pro Leu Pro Gln Gly Gln Leu Thr Ala Tyr
    50                  55                  60

His Val Ser Thr Ala Pro Thr Gly Ser Trp Phe Ser Ala Pro Gln Pro
65                  70                  75                  80

Ala Pro Glu Asn Ala Tyr Gln Ala Tyr Ala Ala Pro Gln Leu Phe Pro
                85                  90                  95

Val Ser Asp Ile Thr Gln Asn Gln Gln Thr Asn Gln Ala Gly Gly Glu

-continued

```
              100                 105                 110
Ala Pro Gln Pro Gly Asp Asn Ser Thr Val Gln Thr Ala Ala Ala Val
            115                 120                 125

Val Phe Ala Cys Pro Gly Ala Asn Gln Gly Gln Gln Leu Ala Asp Ile
        130                 135                 140

Gly Val Pro Gln Pro Ala Pro Val Ala Ala Pro Ala Arg Arg Thr Arg
145                 150                 155                 160

Lys Pro Gln Gln Pro Glu Ser Leu Glu Glu Cys Asp Ser Glu Leu Glu
                165                 170                 175

Ile Lys Arg Tyr Lys Asn Arg Val Ala Ser Arg Lys Cys Arg Ala Lys
            180                 185                 190

Phe Lys Gln Leu Leu Gln His Tyr Arg Glu Val Ala Ala Ala Lys Ser
        195                 200                 205

Ser Glu Asn Asp Arg Leu Arg Leu Leu Leu Lys Gln Met Cys Pro Ser
        210                 215                 220

Leu Asp Val Asp Ser Ile Ile Pro Arg Thr Pro Asp Val Leu His Glu
225                 230                 235                 240

Asp Leu Leu Asn Phe
                245
```